(12) United States Patent
Caniggia et al.

(10) Patent No.: US 6,376,199 B1
(45) Date of Patent: Apr. 23, 2002

(54) METHODS TO DIAGNOSE A REQUIRED REGULATION OF TROPHOBLAST INVASION

(75) Inventors: Isabella Caniggia, Toronto (CA); Martin Post, 328 Wellesley Street East, Toronto (CA), M4X 1H3; Stephen Lye, Toronto (CA)

(73) Assignees: The Hospital for Sick Children (HSC); Mount Sinai Hospital Corporation; Martin Post, all of Toronto (CA)

( * ) Notice: Subject to any disclaimer, the term of this patent is extended or adjusted under 35 U.S.C. 154(b) by 0 days.

(21) Appl. No.: 09/380,662

(22) PCT Filed: Mar. 5, 1998

(86) PCT No.: PCT/CA98/00180

§ 371 Date: Dec. 21, 1999

§ 102(e) Date: Dec. 21, 1999

(87) PCT Pub. No.: WO98/40747

PCT Pub. Date: Sep. 17, 1998

Related U.S. Application Data

(60) Provisional application No. 60/039,919, filed on Mar. 7, 1997.

(51) Int. Cl.$^7$ .................. G01N 33/567; C12Q 1/68; A61K 39/395; A61K 39/42
(52) U.S. Cl. ............... 435/7.2; 435/6; 435/7.1; 424/143.1; 424/145.1; 424/139.1
(58) Field of Search .............. 435/6, 7.1, 7.2; 424/139.1, 143.1, 145.1

(56) References Cited

PUBLICATIONS

Munson et al., Biology of Reproduction, vol. 55, 748–755, 1996.*
C.H. Graham et al.: "Molecular mechanisms controlling trophoblast invasion of the uterus", Trophoblast Research, vol. 7, 1993 PP 237–250.
S. St. Jacques et al.: "Localization of endoglin, a transforming growth factor–bets binding protein, and of CD44 and integrins in placenta during the first trimester of pregancy", Biology of Reproduction, vol. 51, 1994, pp. 405–413.
I. Caniggia et al.: Endoglin regulates trophoblast differentiation along the invasive pathway in human placental villous explants:, Endocrinology, vol. 138, No. 11, Nov. 1, 1997, pp. 4977–4988.
C.H. Graham et al.: "Mechanisms of placental invasion of the uterus and their control", Biochemisry and cell biology, vol. 70, No. 10, Oct. 1, 1992, pp. 867–874.
I. Caniggia et al.: "Endoglin regulates trophoblast invasion in human placental villous tissue explants", Biology of Reproduction, vol. 52, No. supl, Jul. 9, 1997, p. 164.
Cross JC et al. 1994. Science. 266: 1508–1518.
Zhou Y et al. 1993. J. Clin. Invest 91: 950–960.
Aplin JD. 1991. J. Cell Science. 99: 681–692.
Damsky CH et al. 1992. J. Clin. Invest. 89: 210–222.
Bischof P et al. 1993. Eur. J. of Obst. and Gyn. and Repr. Biol. 51: 217–226.
Damsky CH et al. 1994. Development. 120: 3657–3666.
Fisher SJ et al. 1989. J. Cell. Biol. 109: 891–902.
Librach CL et al. 1994. J. Biol. Chem. 269: 17125–17131.
Bass KE et al. 1994. Devel. Biol. 164: 550–561.
Graham CH et al. 1992. Biol. Reprod. 46: 561–572.
Graham CH, Lala PK. 1991. J. Cell. Physiol. 148: 228–234.
Lysiak JJ et al. 1995. Placenta. 16: 221–231.
Irving JA and Lala PK. 1995. Ex. Cell. Res. 217: 419–427.
Cheifetz S et al. 1992. J. Biol. Chem. 267: 19027–19030.
Wrana JL et al. 1994. Nature. 370:341–347.
Mitchell EJ et al. 1992. J. Cell. Physiol. 150: 334–343.
Gougos A et al. 1992. Int. Immunol. 4: 83–92.
Yamashita H et al. 1994. J. Biol. Chem. 269: 1995–2001.
Zhang H et al. 1996. J. Immunol. 156: 565–573.
Lastres P et al. 1996. J. Cell Biol. 133: 1109–1121.
Genbacev O et al. 1992. Placenta. 13: 439–461.
Quackenbush EJ and Letarte M. 1985. J. Immunol. 134: 1276–1285.
Gougos A. and Letarte M. 1990. J. Biol. Chem. 265: 8361–8364.
Malcolm ADB. 1992. Bioch. Soc. Trans. 20: 745–746.
Engvall E and Ruoslahti E. 1977. Int. J. Cancer. 20: 1–5.
Soubiran P et al. 1986. A.J.R.I.M. 12: 118–123.
Feinberg RF et al. 1991. Am. J. Pathol. 138: 537–543.
Vicovac I et al. 1995. Placenta. 16: 41–56.
Feinberg RF et al. 1994. J. Clin. Endocrinol Metab. 78: 1241–1248.
Bischof P et al. 1995. Human Reproduction. 10: 734–742.

* cited by examiner

Primary Examiner—Yvonne Eyler
Assistant Examiner—Janet L. Andres
(74) Attorney, Agent, or Firm—Merchant & Gould P.C.

(57) ABSTRACT

Methods are provided for the diagnosis and treatment of patients with increased risk of preeclampsia. The methods involve measuring levels of TGF-$\beta_3$, receptors of cytokines of the TGβ family, or HIF-1α.

16 Claims, 21 Drawing Sheets

FIG. 1

```
LOCUS       HSTGFB3M    2574 bp    RNA              PRI      12-SEP-1993
DEFINITION  Human mRNA for transforming growth factor-beta 3 (TGF-beta
            3).
ACCESSION   X14149
NID         g37095
KEYWORDS    growth factor; transforming growth factor; transforming
            growth factor-beta 3.
SOURCE      human.
  ORGANISM  Homo sapiens
            Eukaryotae; mitochondrial eukaryotes; Metazoa; Chordata;
            Vertebrata; Eutheria; Primates; Catarrhini; Hominidae;
            Homo.
REFERENCE   1 (bases 1 to 2574)
  AUTHORS   Chen,E.Y.
  TITLE     Direct Submission
  JOURNAL   Submitted (23-MAR-1989) Chen E.Y., Genentech Inc., 460 Pt.
            San Bruno Blvd., San Francisco, CA 94080, USA
REFERENCE   2  (bases 1 to 2574)
  AUTHORS   Derynck,R., Lindquist,P.B., Lee,A., Wen,D., Tamm,J.,
            Graycar,J.L., Rhee,L., Mason,A.J., Miller,D.A.,
            Coffey,R.J., Moses,H.L. and Chen,E.Y.
  TITLE     A new type of transforming growth factor-beta, TGF-beta 3
  JOURNAL   EMBO J. 7 (12), 3737-3743 (1988)
  MEDLINE   89091120
COMMENT     See <J03241> for alternative sequence of TGF-beta 3.
FEATURES            Location/Qualifiers
     source         1..2574
                    /organism="Homo sapiens"
                        /db_xref="taxon:9606"
                        /tissue_type="placenta, ovary glioblastoma"
                        /cell_line="A172 glioblastoma"
                        /chromosome="14q24"
     CDS            254..1492
                        /note="TGF-beta 3 (AA 1-412)"
                        /codon_start=1
                        /db_xref="PID:g37096"
                        /db_xref="SWISS-PROT:P10600"
                    /translation="MKMHLQRALVVLALLNFATVSLSLSTCTTLDFGHIKKKRVEAIR
            GQILSKLRLTSPPEPTVMTHVPYQVLALYNSTRELLEEMHGEREEGCTQENTESEYYA
            KEIHKFDMIQGLAEHNELAVCPKGITSKVFRFNVSSVEKNRTNLFRAEFRVLRVPNPS
            SKRNEQRIELFQILRPDEHIAKQRYIGGKNLPTRGTAEWLSFDVTDTVREWLLRRESN
            LGLEISIHCPCHTFQPNGDILENIHEVMEIKFKGVDNEDDHGRGDLGRLKKQKDHHNP
            HLILMMIPPHRLDNPGQGGQRKKRALDTNYCFRNLEENCCVRPLYIDFRQDLGWKWVH
            EPKGYYANFCSGPCPYLRSADTTHSTVLGLYNTLNPEASASPCCVPQDLEPLTILYYV
            GRTPKVEQLSNMVVKSCKCS"
BASE COUNT       629 a     680 c     666 g     599 t
```

FIG. 1 (cont'd)

```
ORIGIN
    1 cctgtttaga cacatggaca acaatcccag cgctacaagg cacacagtcc gcttcttcgt
   61 cctcagggtt gccagcgctt cctggaagtc ctgaagctct cgcagtgcag tgagttcatg
  121 caccttcttg ccaagcctca gtctttggga tctggggagg ccgcctggtt ttcctccctc
  181 cttctgcacg tctgctgggg tctcttcctc tccaggcctt gccgtccccc tggcctctct
  241 tcccagctca cacatgaaga tgcacttgca aagggctctg gtggtcctgg ccctgctgaa
  301 ctttgccacg gtcagcctct ctctgtccac ttgcaccacc ttggacttcg gccacatcaa
  361 gaagaagagg gtggaagcca ttagggggaca gatcttgagc aagctcaggc tcaccagccc
  421 ccctgagcca acgtgatga cccacgtccc ctatcaggtc ctggcccttt acaacagcac
  481 ccgggagctg ctggaggaga tgcatgggga gagggaggaa ggctgcaccc aggaaaacac
  541 cgagtcggaa tactatgcca aagaaatcca taaattcgac atgatccagg ggctggcgga
  601 gcacaacgaa ctggctgtct gccctaaagg aattacctcc aaggttttcc gcttcaatgt
  661 gtcctcagtg gagaaaaata gaaccaacct attccgagca gaattccggg tcttgcgggt
  721 gcccaacccc agctctaagc ggaatgagca gaggatcgag ctcttccaga tccttcggcc
  781 agatgagcac attgccaaac agcgctatat cggtggcaag aatctgccca cacggggcac
  841 tgccgagtgg ctgtcctttg atgtcactga cactgtgcgt gagtggctgt tgagaagaga
  901 gtccaactta ggtctagaaa tcagcattca ctgtccatgt cacaccttc agcccaatgg
  961 agatatcctg gaaaacattc acgaggtgat ggaaatcaaa ttcaaaggcg tggacaatga
 1021 ggatgaccat ggccgtggag atctggggcg cctcaagaag cagaaggatc accacaaccc
 1081 tcatctaatc ctcatgatga ttcccccaca ccggctcgac aacccgggcc aggggggtca
 1141 gaggaagaag cgggctttgg acaccaatta ctgcttccgc aacttggagg agaactgctg
 1201 tgtgcgcccc ctctacattg acttccgaca ggatctgggc tggaagtggg tccatgaacc
 1261 taagggctac tatgccaact tctgctcagg cccttgccca tacctccgca gtgcagacac
 1321 aacccacagc acggtgctgg gactgtacaa cactctgaac cctgaagcat ctgcctcgcc
 1381 ttgctgcgtg ccccaggacc tggagcccct gaccatcctg tactatgttg ggaggacccc
 1441 caaagtggag cagctctcca acatggtggt gaagtcttgt aaatgtagct gagaccccac
 1501 gtgcgacaga gagaggggag agagaaccac cactgcctga ctgccgctc ctcgggaaac
 1561 acacaagcaa caaacctcac tgagaggcct ggagcccaca accttcggct ccgggcaaat
 1621 ggctgagatg gaggtttcct tttggaacat ttctttcttg ctggctctga gaatcacggt
 1681 ggtaaagaaa gtgtgggttt ggttagagga aggctgaact cttcagaaca cacagacttt
 1741 ctgtgacgca gacagagggg atggggatag aggaagggga tggtaagttg agatgttgtg
 1801 tggcaatggg atttgggcta ccctaaaggg agaaggaagg gcagagaatg gctgggtcag
 1861 ggccagactg gaagacactt cagatctgag gttggatttg ctcattgctg taccacatct
 1921 gctctaggga atctggatta tgttatacaa ggcaagcatt ttttttttta aagacaggtt
 1981 acgaagacaa agtcccagaa ttgtatctca tactgtctgg gattaagggc aaatctatta
 2041 cttttgcaaa ctgtcctcta catcaattaa catcgtgggt cactacaggg agaaaatcca
 2101 ggtcatgcag ttcctggccc atcaactgta ttgggccttt tggatatgct gaacgcagaa
 2161 gaaagggtgg aaatcaaccc tctcctgtct gccctctggg tccctcctct cacctctccc
 2221 tcgatcatat ttccccttgg acacttggtt agacgccttc caggtcagga tgcacatttc
 2281 tggattgtgg ttccatgcag ccttgggca ttatgggtct tccccactt cccctccaag
 2341 accctgtgtt catttggtgt tcctggaagc aggtgctaca acatgtgagg cattcgggga
 2401 agctgcacat gtgccacaca gtgacttggc cccagacgca tagactgagg tataaagaca
 2461 agtatgaata ttactctcaa aatctttgta taaataaata tttttggggc atcctggatg
 2521 atttcatctt ctggaatatt gtttctagaa cagtaaaagc cttattctaa ggtg
//
```

FIG. 2

```
LOCUS       HSU22431    3678 bp    mRNA           PRI      28-JUN-1995
DEFINITION  Human hypoxia-inducible factor 1 alpha (HIF-1 alpha) mRNA, complete
            cds.
ACCESSION   U22431
NID         g881345
KEYWORDS    .
SOURCE      human.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 3678)
  AUTHORS   Wang,G.L., Jiang,B.H., Rue,E.A. and Semenza,G.L.
  TITLE     Hypoxia-inducible factor 1 is a basic-helix-loop-helix-PAS
            heterodimer regulated by cellular O2 tension
  JOURNAL   Proc. Natl. Acad. Sci. U.S.A. 92 (12), 5510-5514 (1995)
  MEDLINE   95296340
REFERENCE   2  (bases 1 to 3678)
  AUTHORS   Wang,G.L., Jiang,B.-H., Rue,E.A. and Semenza,G.L.
  TITLE     Direct Submission
  JOURNAL   Submitted (09-MAR-1995) Gregg L. Semenza, Center for Medical
            Genetics, The Johns Hopkins University School of Medicine, 600 N.
            Wolfe St., Baltimore, MD 21287-3914, USA
FEATURES             Location/Qualifiers
     source          1..3678
                     /organism="Homo sapiens"
                     /db_xref="taxon:9606"
                     /cell_line="Hep3B"
                     /cell_type="hepatoblastoma"
     gene            29..2509
                     /gene="HIF-1 alpha"
     CDS             29..2509
                     /gene="HIF-1 alpha"
                     /standard_name="hypoxia-inducible factor 1, alpha subunit"
                     /note="basic helix-loop-helix transcription factor"
                     /codon_start=1
                     /product="hypoxia-inducible factor 1 alpha"
                     /db_xref="PID:g881346"
                     /translation="MEGAGGANDKKKISSERRKEKSRDAARSRRSKESEVFYELAHQL
                     PLPHNVSSHLDKASVMRLTISYLRVRKLLDAGDLDIEDDMKAQMNCFYLKALDGFVMV
                     LTDDGDMIYISDNVNKYMGLTQFELTGHSVFDFTHPCDHEEMREMLTHRNGLVKKGKE
                     QNTQRSFFLRMKCTLTSRGRTMNIKSATWKVLHCTGHIHVYDTNSNQPQCGYKKPPMT
                     CLVLICEPIPHPSNIEIPLDSKTFLSRHSLDMKFSYCDERITELMGYEPEELLGRSIY
                     EYYHALDSDHLTKTHHDMFTKGQVTTGQYRMLAKRGGYVWVETQATVIYNTKNSQPQC
                     IVCVNYVVSGIIQHDLIFSLQQTECVLKPVESSDMKMTQLFTKVESEDTSSLFDKLKK
                     EPDALTLLAPAAGDTIISLDFGSNDTETDDQQLEEVPLYNDVMLPSPNEKLQNINLAM
                     SPLPTAETPKPLRSSADPALNQEVALKLEPNPESLELSFTMPQIQDQTPSPSDGSTRQ
                     SSPEPNSPSEYCFYVDSDMVNEFKLELVEKLFAEDTEAKNPFSTQDTDLDLEMLAPYI
                     PMDDDFQLRSFDQLSPLESSSASPESASPQSTVTVFQQTQIQEPTANATTTTATTDEL
                     KTVTKDRMEDIKILIASPSPTHIHKETTSATSSPYRDTQSRTASPNRAGKGVIEQTEK
                     SHPRSPNVLSVALSQRTTVPEEELNPKILALQNAQRKRKMEHDGSLFQAVGIGTLLQQ
                     PDDHAATTSLSWKRVKGCKSSEQNGMEQKTIILIPSDLACRLLGQSMDESGLPQLTSY
                     DCEVNAPIQGSRNLLQGEELLRALDQVN"
     polyA_site      3678
                     /note="42 A nucleotides"
BASE COUNT    1197 a    695 c    675 g   1111 t
```

FIG. 2 (cont'd)

```
ORIGIN
    1 gtgaagacat cgcggggacc gattcaccat ggagggcgcc ggcggcgcga acgacaagaa
   61 aaagataagt tctgaacgtc gaaaagaaaa gtctcgagat gcagccagat ctcggcgaag
  121 taaagaatct gaagtttttt atgagcttgc tcatcagttg ccacttccac ataatgtgag
  181 ttcgcatctt gataaggcct ctgtgatgag gcttaccatc agctatttgc gtgtgaggaa
  241 acttctggat gctggtgatt tggatattga agatgacatg aaagcacaga tgaattgctt
  301 ttatttgaaa gccttggatg gttttgttat ggttctcaca gatgatggtg acatgattta
  361 catttctgat aatgtgaaca aatacatggg attaactcag tttgaactaa ctggacacag
  421 tgtgtttgat tttactcatc catgtgacca tgaggaaatg agagaaatgc ttacacacag
  481 aaatggcctt gtgaaaaagg gtaaagaaca aaacacacag cgaagctttt ttctcagaat
  541 gaagtgtacc ctaactagcc gaggaagaac tatgaacata aagtctgcaa catggaaggt
  601 attgcactgc acaggccaca ttcacgtata tgataccaac agtaaccaac ctcagtgtgg
  661 gtataagaaa ccacctatga cctgcttggt gctgatttgt gaacccattc ctcacccatc
  721 aaatattgaa attcctttag atagcaagac tttcctcagt cgacacagcc tggatatgaa
  781 attttcttat tgtgatgaaa gaattaccga attgatggga tatgagccag aagaactttt
  841 aggccgctca atttatgaat attatcatgc tttggactct gatcatctga ccaaaactca
  901 tcatgatatg tttactaaag gacaagtcac cacaggacag tacaggatgc ttgccaaaag
  961 aggtggatat gtctgggttg aaactcaagc aactgtcata tataacacca agaattctca
 1021 accacagtgc attgtatgtg tgaattacgt tgtgagtggt attattcagc acgacttgat
 1081 tttctccctt caacaaacag aatgtgtcct taaaccggtt gaatcttcag atatgaaaat
 1141 gactcagcta ttcaccaaag ttgaatcaga agatacaagt agcctcttgt acaaacttaa
 1201 gaaggaacct gatgctttaa ctttgctggc cccagccgct ggagacacaa tcatatcttt
 1261 agattttggc agcaacgaca cagaaactga tgaccagcaa cttgaggaag taccattata
 1321 taatgatgta atgctcccct cacccaacga aaaattacag aatataaatt tggcaatgtc
 1381 tccattaccc accgctgaaa cgccaaagcc acttcgaagt agtgctgacc ctgcactcaa
 1441 tcaagaagtt gcattaaaat tagaaccaaa tccagagtca ctggaacttt cttttaccat
 1501 gccccagatt caggatcaga cacctagtcc ttccgatgga agcactagac aaagttcacc
 1561 tgagcctaat agtcccagtg aatattgttt ttatgtggat agtgatatgg tcaatgaatt
 1621 caagttggaa ttggtagaaa aacttttttgc tgaagacaca gaagcaaaga acccatttttc
 1681 tactcaggac acagatttag acttggagat gttagctccc tatatcccaa tggatgatga
 1741 cttccagtta cgttcccttcg atcagttgtc accattagaa agcagttccg caagccctga
 1801 aagcgcaagt cctcaaagca cagttacagt attccagcag actcaaatac aagaacctac
 1861 tgctaatgcc accactacca ctgccaccac tgatgaatta aaaacagtga caaaagaccg
 1921 tatggaagac attaaaatat tgattgcatc tccatctcct acccacatac ataaagaaac
 1981 tactagtgcc acatcatcac catatagaga tactcaaagt cggacagcct caccaaacag
 2041 agcaggaaaa ggagtcatag aacagacaga aaaatctcat ccaagaagcc ctaacgtgtt
 2101 atctgtcgct ttgagtcaaa gaactacagt tcctgaggaa gaactaaatc aaagatact
 2161 agctttgcag aatgctcaga gaaagcgaaa aatggaacat gatggttcac tttttcaagc
 2221 agtaggaatt ggaacattat tacagcagcc agacgatcat gcagctacta catcacttttc
 2281 ttggaaacgt gtaaaaggat gcaaatctag tgaacagaat ggaatggagc aaaagacaat
 2341 tattttaata ccctctgatt tagcatgtag actgctgggg caatcaatgg atgaaagtgg
 2401 attaccacag ctgaccagtt atgattgtga agttaatgct cctatacaag gcagcagaaa
 2461 cctactgcag ggtgaagaat tactcagagc tttggatcaa gttaactgag cttttctta
 2521 atttcattcc ttttttttgga cactggtggc tcactaccta aagcagtcta tttatatttt
 2581 ctacatctaa ttttagaagc ctggctacaa tactgcacaa acttggttag ttcaattttt
 2641 gatcccctttt ctacttaatt tacattaatg ctctttttta gtatgttctt taatgctgga
 2701 tcacagacag ctcatttttct cagttttttg gtatttaaac cattgcattg cagtagcatc
 2761 attttaaaaa atgcaccttt ttatttattt attttttggct agggagttta tccctttttc
 2821 gaattatttt taagaagatg ccaatataat ttttgtaaga aggcagtaac ctttcatcat
 2881 gatcataggc agttgaaaaa ttttttacacc ttttttttca catttttacat aaataataat
 2941 gctttgccag cagtacgtgg tagccacaat tgcacaatat attttcttaa aaaataccag
 3001 cagttactca tggaatatat tctgcgttta taaaactagt ttttaagaag aaatttttttt
 3061 tggcctatga aattgttaaa cctggaacat gacattgtta atcatataat aatgattctt
 3121 aaatgctgta tggtttatta tttaaatggg taaagccatt tacataatat agaaagatat
 3181 gcatatatct agaaggtatg tggcatttat ttggataaaa ttctcaattc agagaaatca
 3241 tctgatgttt ctatagtcac tttgccagct caaaagaaaa caatacccta tgtagttgtg
 3301 gaagtttatg ctaatattgt gtaactgata ttaaacctaa atgttctgcc tacccctgttg
 3361 gtataaagat attttgagca gactgtaaac aagaaaaaaa aaatcatgca ttcttagcaa
 3421 aattgcctag tatgttaattt tgctcaaaat acaatgtttg attttatgca ctttgtcgct
 3481 attaacatcc ttttttttcat gtagatttca ataattgagt aattttagaa gcattatttt
 3541 aggaatatat agttgtcaca gtaaatatct tgttttttct atgtacattg tacaaatttt
 3601 tcattccttt tgctctttgt ggttggatct aacactaact gtattgtttt gttacatcaa
 3661 ataaacatct tctgtgga
```

Gestational age (weeks)

FIG. 3B
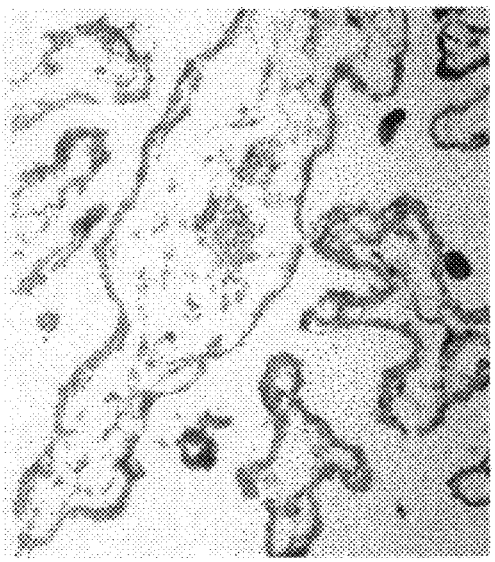
5 weeks
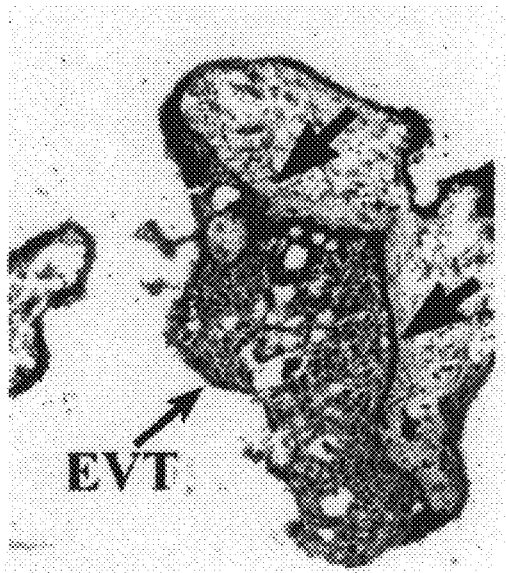
8 weeks
12 weeks
8 weeks (control)

Normal Placenta            Preeclamptic placenta

S-ß3            S-ß3            AS-ß3

FIG. 9
20% O2
25X
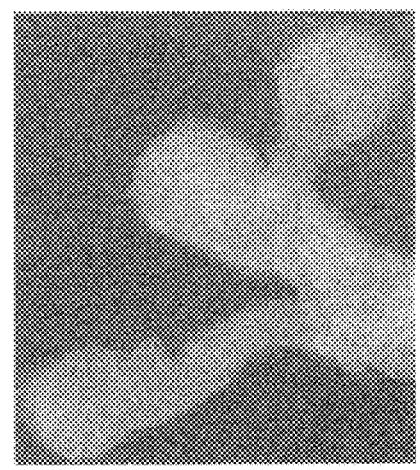
50X
3% O2
25X
50X

FIG. 10
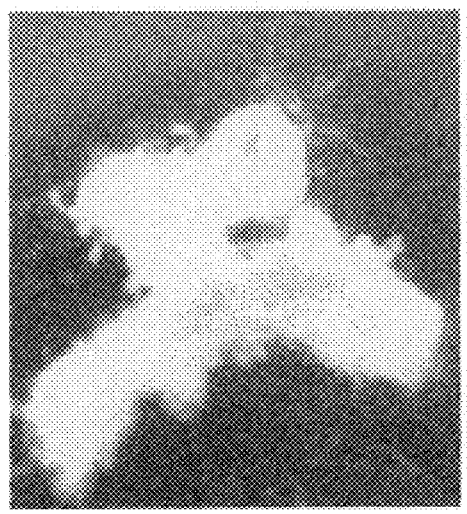
S-HIF
20X
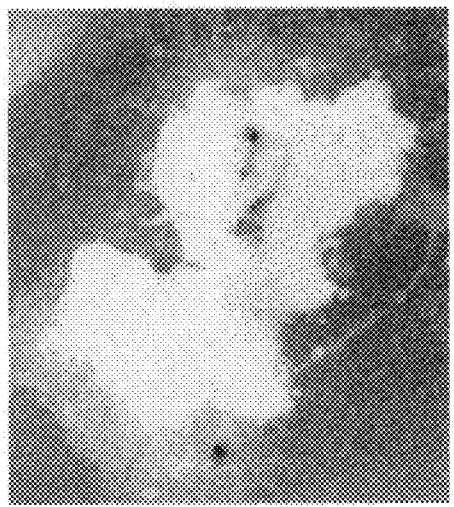
AS-HIF
20X
AS-HIF
40X
AS-HIF
40X

METHODS TO DIAGNOSE A REQUIRED REGULATION OF TROPHOBLAST INVASION

This application claims the benefit of provisional No. 60/039,919 filed Mar. 7, 1997.

FIELD OF THE INVENTION

The invention relates to methods and compositions for diagnosing and treating conditions requiring regulation of trophoblast invasion.

BACKGROUND OF THE INVENTION

During placental development the establishment of fetal-maternal interactions is critical for a successful human pregnancy (1). Abnormalities of placenta formation due to shallow trophoblast invasion have been linked to preeclampsia and fetal growth restriction (2). In contrast, uncontrolled trophoblast invasion and abnormal trophoblast growth are associated with hydatiform mole and choriocarcinoma. In the course of placenta formation, chorionic villous cytotrophoblasts undergo two morphologically distinct pathways of differentiation. The vast majority of cytotrophoblasts in both floating and anchoring villi fuse to form the syncytiotrophoblast layer, which permits gas and nutrient exchange for the developing embryo. A small percentage of cytotrophoblasts in anchoring villi break through the syncytium, at selected sites, and generate columns of non-polarized cells which migrate into the endometrium. These extravillous trophoblasts (EVT) invade deeply into the uterus reaching the first third of the myometrium at which point they invade the spiral arteries, replacing their endothelium and vascular wall. Invasion peaks at 12 weeks of gestation and rapidly declines thereafter. indicating that, unlike tumour invasion, it is spatially and temporally regulated (3). Trophoblast invasion in the decidua is accompanied by a complex modulation of the synthesis and degradation of extracellular matrix (ECM) proteins and in the expression of adhesion molecules (4–6). Along the invasive pathway, ECM proteins undergo changes in their spatial distribution with loss of laminin and appearance of fibronectin (3,4). EVT loose the expression of E-cadherins, responsible for cell-cell adhesion between polarized stem cytotrophoblasts, down-regulate $\alpha_6\beta_4$ integrin, a laminin receptor, and acquire $\alpha_5\beta_1$ integrin, a fibronectin recepor (7). Once the EVT invade the endometrium they express the $\alpha_1\beta_1$ integrin, a collagen/laminin receptor. Thus, specific changes in ECM proteins and their receptors are associated with the acquisition of an invasive phenotype by the extravillous trophoblasts (4).

Preeclampsia occurs in 5–10% of pregnancies and is the leading cause of death and illness in women during pregnancy. Preeclamnpsia is also associated with considerable fetal/neonatal complications because of adverse intrauterine conditions and preterm delivery. There is currently no effective pharmacologic treatment for preeclampsia and the only remedy is to remove the placenta (and hence deliver the fetus preterm). Current protocols, including bedrest and antihypertensive drugs, seek to stabilize maternal/fetal condition until delivery is necessitated. It is estimated that around 200,000 children are born preterm in North America due to preeclampsia. Many of these babies will require costly intensive care at birth and if they survive may face a lifetime of chronic illness (e.g. lung disease) or disability (e.g. cerebral palsy, mental handicaps, blindness). These conditions represent a significant impact on subsequent requirements for community health care resources. Therefore, reducing the incidence of preeclampsia and preterm birth would have a tremendous positive impact on health care delivery.

SUMMARY OF THE INVENTION

The present inventors have studied the mechanisms that regulate trophoblast invasion. The inventors have found that antisense disruption of the expression of the TGFβ receptor, endoglin, triggers invasion of cytotrophoblast from first trimester villous explants in vitro indicating that the TGFβ receptor system, and in particular endoglin, plays a critical role in regulating this process. Significantly, the present inventors defined components that endogenously regulate trophoblast invasion. TGF-$\beta_3$ was found to be a major regulator of trophoblast invasion in vitro. In particular, the presence of TGF-$\beta_3$ and its receptors at 5–8 weeks at a time when there is no spontaneous trophoblast invasion and the absence of these molecules at 12–13 weeks when spontaneous invasion occurs, establishes a major role for TGF-$\beta_3$ as an endogenous inhibitor of trophoblast invasion. Down-regulation of TGF-$\beta_3$ (but not $\beta_1$ or $\beta_2$) expression using antisense oligonucleotides, stimulated extravillous trophoblast cell (EVT) outgrowth/migration and fibronectin production in 5–8 villous explants indicating that TGF-$\beta_3$ acts to suppress in vivo trophoblast invasion. The effects of antisense treatment to TGF-$\beta_3$ are specific as they are prevented by addition of exogenous TGF-$\beta_3$ but not TGF-$\beta_1$ or TGF-$\beta_2$. The stimulatory effects of TGF-$\beta_3$ are lost after 9 weeks of gestation which is compatible with TGF-$\beta_3$ being produced by the villi during a specific window of gestation within the first trimester (5–8 weeks) and that inhibition of its synthesis stimulates trophoblast differentiation. Addition of exogenous TGF-$\beta_3$ to the villous explants inhibits fibronectin synthesis.

The clinical importance of TGF-$\beta_3$ in regulating trophoblast invasion has been highlighted by the finding that TGF-$\beta_3$ is highly expressed in trophoblast tissue of preeclamptic patients when compared to that in age-matched control placenta while there was no change in the expression of either the $\beta_1$ or $\beta_2$ isoform. Fibronectin and $\alpha_5$ integrin expression were also greater in preeclamptic placenta, indicating that in preeclampsia, where there is shallow trophoblast invasion, trophoblast cells are arrested as an $\alpha_5$ integrin phenotype producing TGF-$\beta_3$. These data are supported by the finding that villous explants from a control (non-preeclamptic placenta, 32 weeks of gestation) spontaneously formed columns of trophoblasts that invaded the surrounding Matrigel, while explants from a preeclamptic placenta did not.

In contrast to TGF-$\beta_3$, activin, a TGF-$\beta$ receptor, has been found to trigger trophoblast invasion. Follistatin an activin binding protein, inhibited the stimulatory effect of activin, and antibodies and antisense to endoglin.

Oxygen tension was also found to play a role in regulating trophoblast invasion. The expression of the hypoxia inducible factor, HIF-1$\alpha$, parallels that of TGF-$\beta_3$ in first trimester trophoblast (i.e. peaks at 6–8 weeks but decreases after 9–10 weeks when oxygen tension increases). Expression of HIF-1$\alpha$ was dramatically increased in placentas of preeclamptic patients when compared to age-matched control tissue. Induction of HIF-1$\alpha$ by low PO$_2$ (around 6–8 weeks) up regulates TGF-$\beta_3$ transcription and blocks trophoblast invasion. A failure of the system to down-regulate at 9–11 weeks (either due to a block in response to normoxia or the absence of an increase in oxygen tension) leads to shallow invasion and predisposes to preeclampsia.

In addition to endoglin, the present inventors have found that TGF-$\beta_3$ signals through a receptor complex which includes RI (ALK1), RII and endoglin. While TGF-$\beta$ RI (ALK-5) and TGF-$\beta$ R-II are expressed throughout the villi and decidua at 9–10 weeks gestation, they were found to be absent from the base of the proximal columns of the anchoring villi at the transition zone between the villous and the invading EVT exactly at the site where endoglin is up-regulated. This dramatic change in TGF-$\beta$ receptor expression indicates that EVT within the columns in situ are not subject to the inhibitory actions of TGF$\beta$, but via R-I and R-II they come under the control of this ligand upon entering the decidua. In addition, antisense induced disruption of RI (ALK-1) and RII expression stimulated trophoblast outgrowth/migration and fibronectin synthesis. In contrast, antisense to RI (ALK-5) inhibited fibronectin synthesis.

Broadly stated the present invention relates to a method for detecting, preventing, and/or treating a condition requiring regulation of trophoblast invasion by modulating (a) TGF$\beta_3$ (b) receptors of cytokines of the TGF$\beta$ family, (c) HIF-1$\alpha$, and/or (d) $O_2$ tension. In accordance with one aspect of the invention a method is provided for diagnosing in a subject a condition requiring regulation of trophoblast invasion comprising detecting TGF$\beta_3$, receptors of cytokines of the TGF$\beta$ family, or HIF-1$\alpha$, in a sample from the subject. In an embodiment of the diagnostic method of the invention, a method is provided for diagnosing increased risk of preeclampsia in a subject comprising detecting TGF$\beta_3$ or its receptors, or HIF-1$\alpha$ in a sample from the subject.

The invention also broadly contemplates a method for regulating trophoblast invasion comprising inhibiting or stimulating TGF$\beta_3$, receptors of cytokines of the TGF$\beta$ family. HIF-1$\alpha$ or $O_2$ tension. In an embodiment of the invention, a method is provided for increasing trophoblast invasion in a subject comprising administering to the subject an effective amount of an inhibitor of (a) TGF$\beta_3$, (b) receptors of cytokines of the TGF$\beta$ family, and/or (c) HIF-1$\alpha$. In a preferred embodiment of the invention a method is provided for treating a woman suffering from, or who may be susceptible to preeclampsia comprising administering therapeutically effective dosages of an inhibitor of (a) TGF$\beta_3$, (b) receptors of cytokines of the TGF$\beta$ family, and/or (c) HIF-1$\alpha$. A therapeutically effective dosage is an amount of an inhibitor of (a), (b) and/or (c) effective to down regulate or inhibit TGF$\beta_3$ in the woman.

In another embodiment of the invention, a method is providing for reducing trophoblast invasion in a subject comprising administering an effective amount of (a) TGF$\beta_3$; (b) receptors of cytokines of the TGF$\beta$ family; (c) HIF-1$\alpha$; and/or (d) a stimulator of (a), (b) or (c). In a preferred embodiment, a method is provided for monitoring or treating choriocarcinoma or hydatiform mole in a subject comprising administering therapeutically effective dosages of (a) TGF$\beta_3$; (b) receptors of cytokines of the TGF$\beta$ family; (c) HIF-1$\alpha$; and/or (d) a stimulator of (a), (b) or (c). An amount is administered which is effective to up regulate or stimulate TGF$\beta_3$ in the subject.

The invention also relates to a composition adapted for regulating trophoblast invasion comprising a substance which inhibits or stimulates TGF$\beta_3$ receptors of cytokines of the TGF$\beta$ family, and/or HIF-1$\alpha$, or regulates $O_2$ tension, in an amount effective to inhibit or stimulate trophoblast invasion, and an appropriate carrier, diluent, or excipient. In an embodiment of the invention, a composition is provided for treating a woman suffering from, or who may be susceptible to preeclampsia, comprising a therapeutically effective amount of an inhibitor of (a) TGF$\beta_3$, (b) receptors of cytokines of the TGF$\beta$ family, and/or (c) HIF-1$\alpha$, and a carrier, diluent, or excipient. In another embodiment of the invention, a composition is provided for monitoring or treating choriocarcinoma or hydatiform mole in a subject comprising a therapeutically effective amount of (a) TGF$\beta_3$; (b) receptors of cytokines of the TGF$\beta$ family; (c) HIF-1$\alpha$; and/or (d) a stimulator of (a), (b) or (c), and a carrier, diluent, or excipient.

The invention further relates to a method of selecting a substance that regulates trophoblast invasion comprising assaying for a substance that inhibits or stimulates TGF$\beta_3$, receptors of a cytokine of the TGF$\beta$ family, or HIF-1$\alpha$. The substances may be used in the methods of the invention to regulate trophoblast invasion.

The invention also relates to kits for carrying out the methods of the invention.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 shows the amino acid and nucleic acid sequence of TGF$\beta$3 (SEQ ID NO:21 and SEQ ID NO:20);

FIG. 2 shows the amino acid and nucleic acid sequence of HIF-1$\alpha$ (SEQ ID NO:23 and SEQ ID NO:22);

FIG. 3B are photographs of immunoperoxidase staining of TGF$\beta_3$ performed in placental sections at 5, 8, and 12 weeks of gestation;

FIG. 9 are photographs at 20% O$_2$ and 3% O$_2$ (25× and 50×) showing the effect of low oxygen tension on villous explant morphology; and FIG. 10 are photographs showing the effect of antisense to HIF-1α on villous explant morphology.

DETAILED DESCRIPTION OF THE INVENTION

1. Diagnostic Methods

Figure 3A:
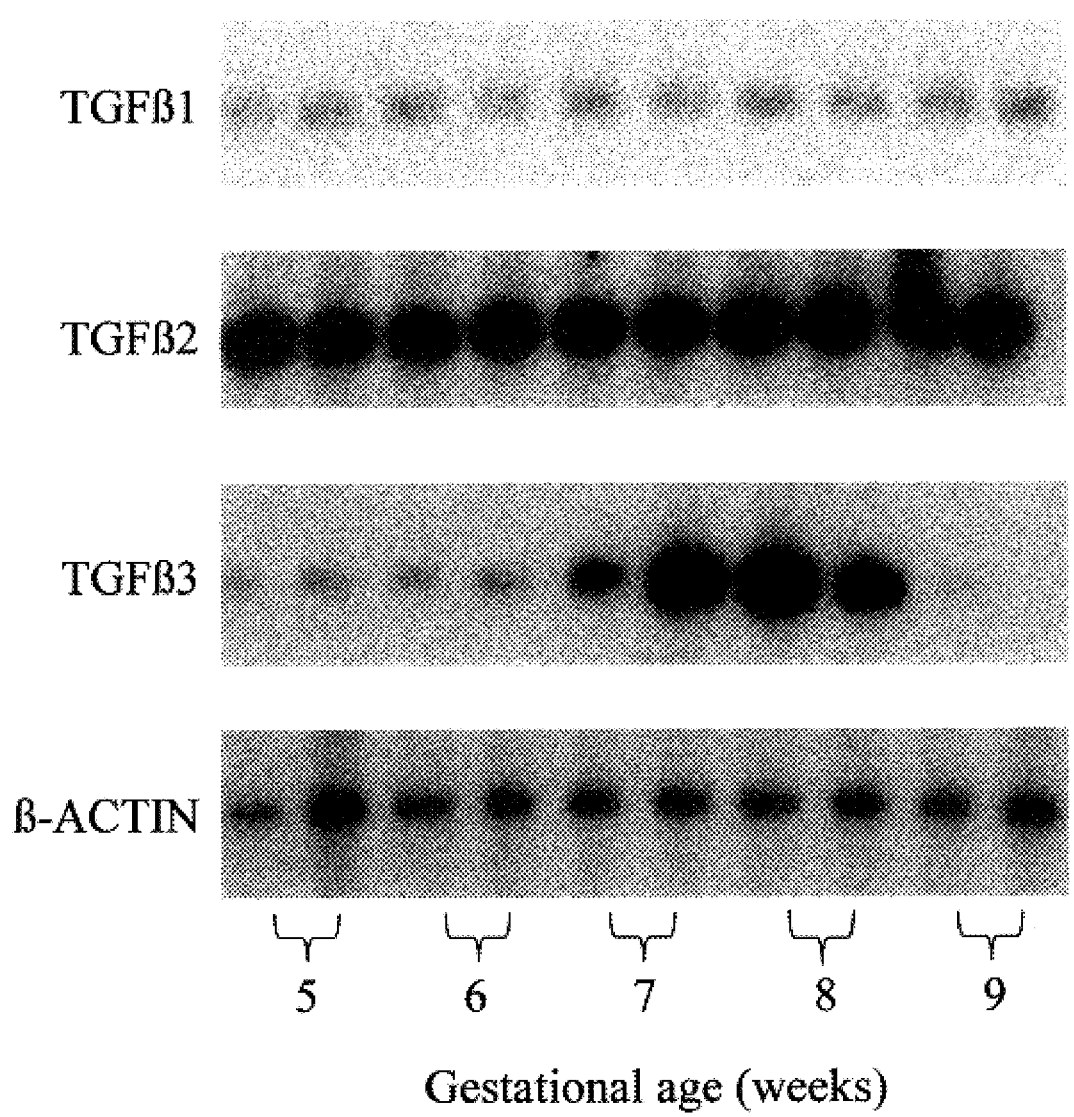
FIG. 3A are Southern blots showing expression of TGF-$\beta$ isoforms in human placenta in the first trimester of gestation.

As hereinbefore mentioned, the present invention provides a method for diagnosing in a subject a condition requiring regulation of trophoblast invasion comprising detecting TGFβ$_3$, receptors of cytokines of the TGFβ family, or HIF-1α in a sample from the subject. In an embodiment of the diagnostic method of the invention, a method is provided for diagnosing increased risk of preeclampsia in a subject comprising detecting TGFβ$_3$, its receptors, or HIF-1α in a sample from the subject.

TGFβ$_3$ is a cytokine of the TGFβ family and it has the structural characteristics of the members of the TGFβ family. TGFβ is produced as a precursor characterised by having an N-terminal hydrophobic signal sequence for translocation across the endoplasmic reticulum, a pro-region, and a C-terminal bioactive domain. Prior to release from the cell, the pro-region is cleaved at a site containing four basic amino acids immediately preceding the bioactive domain (Massague, 1990, Annu.Review. Cell Biol. 6:597).

The precursor structure of TGFβ is shared by members of the TGFβ family, with the exception of the TGFβ 4 precursor which lacks a distinguishable signal sequence. The degree of identity between family members in the C-terminal bioactive domain is from 25 to 90% (See Basler et al. Cell, 73:687, 1993, FIG. 2). All nine cysteines are conserved in the bioactive domain in the TGFβ family. The bioactive domain is cleaved to generate a mature monomer.

The TGFβ family includes five members, termed TGFβ 1 through TGFβ 5, all of which form homodimers of about 25 kd (reviewed in Massague, 1990). The family also includes TGFβ 1.2 which is a heterodimer containing a β1 and a β2 subunit linked by disulfide bonds. The five TGFβ genes are highly conserved. The mature TGFβ processed cytokines produced from the members of the gene family show almost 100% amino acid identity between species, and the five peptides as a group show about 60–80% identity. The amino acid sequence and nucleic acid sequence of TGFβ$_3$, are shown in FIG. 1 (SEQ ID NO:21 and SEQ ID NO:20) (See also sequences for GenBank Acession Nos. HSTGF31–HSTGF37, and HSTGFB3M).

"Receptors of cytokines of the TGFβ family" or "TGFβ receptors" refers to the specific cell surface receptors which bind to cytokines of the TGFβ family, in particular TGFβ$_3$, including the TGF-β type I receptor (ALK-1 or ALK-5) (R-I), TGF-β type II receptor (R-II), betaglycan, endoglin and activin, and complexes of the receptors, in particular a RI-RII-endoglin complex. Endoglin binds TGFβ$_1$ and β$_3$ with high affinity ($K_D$=50 pM). Betaglycan has considerable sequence homology to endoglin (Chiefetz, S., et al J. Biol Chem. 267: 19027, 1992; Lopez-Casillas, F., et al, Cell 67:785, 1991; Wang, X. F., et al, Cell 67:797, 1991), it can bind all three forms of TGFβ$_3$, and it regulates access of the ligands to R-I and R-II which are serine/threonine kinases and unlike betaglycan, are necessary for signal transduction (Wrana, J. L. et al, Cell 71:1003, 1992, Lopez-Casillas et al. Cell 73:1435, 1993; Franzen, P., et al Cell 75:681, 1993; Laiho, M. et al, J. Biol. Chem. 266:9108; Massague, J. et al, Trends Cell Biol. 4:172, 1994). TGFβR-II is an integral membrane protein which contains a short extracellular domain, a single transmembrane domain, and an intracellular serine/threonine kinase domain (Lin H. Y. et al., Cell 68:775, 1992). Serine/threonine kinases encoding type II receptors have been cloned which are structurally related to the type II receptors (Wrana, J. L et al, Cell 71:1003, 1992, ten Dikje, P., et al. Oncogene 8:2879, 1993; Ebner, R., et al Science 260:1344, 1993; Ebner, R., et al Science 262:900, 1993). TGFβ R-I (human ALK-5), binds TGFβ$_1$ and β$_3$ only in the presence of TGFβ R-II (Wrana, J. L. et al, Cell 71:1003, 1992). The human ALK-1 (TGFβ R-I) binds TGFβ when forming a heterodimeric complex with TGFβ R-II (Franzen, P., et al Cell 75:681, 1993). TGFβ R-II kinase, which is endogenously phosphorylated, phosphorylates and activates R-I which then initiates further downstream signals (Wrana, J. L. et al, Nature 370:341, 1994).

Hypoxia-inducible factor-I (HIF-I) is present in nuclear extracts of many mammalian cells cultivated in a low oxygen atmosphere (Semenza, G. L. et al Mol. Cell. Biol. 12:5447, 1992; Wang, G. L. J. Biol. Chem. 268:21513, 1993). HIF-I binds as a phosphoprotein to a short DNA motif (BACGTSSK) (SEQ ID NO:24) identified in the 3-flanking regions of many hypoxia-induced genes (Semenza, G. L. et al. J. Biol Chem 269:23757, 1994; Liu, Y., et al Circulation Res. 77:638, 1995; Firth, J. D. et al Proc. Natl. Acad. Sci. USA 91:6496, 1994; Abe, M., et al. Anal. Biochem. 216:276, 1994). HIF-I binds DNA as a heterodimeric complex composed of two subunits of the inducible HIF-1α and the constitutively expressed HIF-Iβ.

TGFβ$_3$, receptors of cytokines of the TGFβ family (e.g.TGFβ RI (ALK-1). TGFβ RII, or a complex of RI-RII-endoglin), or HIF-1α may be detected in a variety of samples from a patient. Examples of suitable samples include cells (e.g. fetal or maternal); and, fluids (fetal or maternal), including for example, serum, plasma, amniotic fluid, saliva, and conditioned medium from fetal or maternal cells.

TGFβ$_3$, receptors of cytokines of the TGFβ family, or HIF-1α may be detected using a substance which directly or indirectly interacts with the cytokine, TGFβ receptors, or HIF-1α. For example, antibodies specific for TGFβ$_3$, the TGFβ receptors, or HIF-1α may be used to diagnose and monitor a condition requiring regulation of trophoblast invasion. A method of the invention using antibodies may utilize Countercurrent immuno-Electrophoresis (CIEP), Radioimmunoassays, Radioimmunoprecipitations, and Enzyme-Linked Immuno-Sorbent Assays (ELISA), Dot Blot assays, Inhibition or Competition assays and sandwich assays (see U.S. Pat. Nos. 4,376,110 and 4,486,530).

Antibodies used in the methods of the invention include monoclonal antibodies, polygonal antibodies, antibody fragments (e.g., Fab, and F(ab')$_2$ and recombinantly produced binding partners. Polyclonal antibodies may be readily generated by one of ordinary skill in the art from a variety of warm-blooded animals such as horses, cows, various fowl, rabbits, mice, or rats. Monoclonal antibodies may also be readily generated using conventional techniques (see U.S. Pat. Nos. RE 32,011, 4,902,614, 4,543,439, and 4,411,993 which are incorporated herein by reference: see also Monoclonal Antibodies, Hybridomas: A New Dimension in Biological Analyses, Plenum Press, Kennett, McKearn and Bechtol (eds.), 1980, and Antibodies: A Laboratory Manual, Harlow and Lane (eds.), Cold Spring Harbor Laboratory Press, 1988, which are also incorporated herein by reference). Binding partners may be constructed utilizing recombinant DNA techniques to incorporate the variable regions of a gene which encodes a specifically binding antibody (See Bird et al. Science 242:423–426, 1988).

Antibodies may also be obtained from commercial sources. For example, antibodies to TGFβ$_3$ may be obtained from American Diagnostics Inc., Connecticut, USA, Oncogene Science, New York, USA, and Dimension Laboratories, Mississauga, Canada.

The presence of TGFβ$_3$ in a sample may also be determined by measuring the binding of the cytokine to compounds which are known to interact with TGFβ$_3$ such as its receptors, or decorin, thrombospondin, the serum glycoprotein α2-macroglobulin, fetuin, or thyroglobulin (Y. Yamaguchi, D. M. Mann, E. Ruoslahti, Nature 346, 281 (1990): S. Scholtz-Cherry J. E. Murphy-Ullrich, *J. Cell Biol.* 122, 923 (1993); O'Conner-McCourt, L. M. Wakefield *J. Biol. Chem.* 262, 14090 (1987); and J. Massague *Curr. Biol.* 1, 117 (1991)). These compounds are referred to herein as "TGFβ Binding Compounds".

The presence of receptors of cytokines of the TGFβ family may be determined by measuring the binding of the receptors to molecules (or parts thereof) which are known to interact with the receptors such as their ligands. In particular, peptides derived from sites on ligands which bind to the receptors may be used. A peptide derived from a specific site on a ligand may encompass the amino acid sequence of a naturally occurring binding site, any portion of that binding site, or other molecular entity that functions to bind an associated molecule. A peptide derived from such a site will interact directly or indirectly with an associated receptor molecule in such a way as to mimic the native binding site. Such peptides may include competitive inhibitors, enhancers, peptide mimetics, and the like as discussed below.

The presence of HIF-1α may be determined by measuring the binding of HIF-α1 to DNA molecules which are known to interact with HIF-α1 such as hypoxia inducing genes. The TGFβ binding compounds and molecules that interact with the receptors and HIF-1α are referred to herein as "Binding Compounds".

The antibodies specific for the TGFβ$_3$, TGFβ receptors, or HIF-1α, or the Binding Compounds may be labelled using conventional methods with various enzymes, fluorescent materials, luminescent materials and radioactive materials. Examples of suitable enzymes include horseradish peroxidase, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an examaple of a luminescent material includes luminol; and examples of suitable radioactive materials include radioactive phosphorous $^{32}$P, iodine $I^{125}$, $I^{131}$ or tritium.

An antibody to TGFβ$_3$, a TGFβ family receptor, or HIF-1α, or a Binding Compound may also be indirectly labelled with a ligand binding partner. For example, the antibodies, or a TGFβ$_3$ Binding Compound may be conjugated to one partner of a ligand binding pair, and the TGFβ$_3$ may be coupled to the other partner of the ligand binding pair. Representative examples include avidin-biotin, and riboflavin-riboflavin binding protein. Preferably the antibodies are biotinylated. Methods for conjugating the antibodies discussed above with the ligand binding partner may be readily accomplished by one of ordinary skill in the art (see Wilchek and Bayer, "The Avidin-Biotin Complex in Bioanalytical Applications," AnaL Biochem. 171:1–32, 1988).

The antibodies or Binding Compounds used in the method of the invention may be insolubilized. For example, the antibodies or Binding Compounds may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinylether-maleic acid copolymer, amino acid copolymer, ethylene-maleic acid copolymer, nylon, silk, etc. The carrier may be in the shape of, for example, a tube, test plate, beads, disc, sphere etc. The insolubilized compound or antibodies may be prepared by reacting the material with a suitable insoluble carrier using known chemical or physical methods, for example, cyanogen bromide coupling.

Indirect methods may also be employed in which a primary antigen-antibody reaction is amplified by the introduction of a second antibody, having specificity for the antibody reactive against the cytokine. By way of example, if the antibody having specificity against TGFβ$_3$ is a rabbit IgG antibody, the second antibody may be goat anti-rabbit gamma-globulin labelled with a detectable substance as described herein.

TGFβ$_3$, TGFβ receptors, or HIF-1α can also be assayed in a sample using nucleotide probes to detect nucleic acid molecules encoding a TGFβ$_3$, the TGFβ receptors, or HIF-1α. Suitable probes include nucleic acid molecules based on nucleic acid sequences encoding TGFβ$_3$, the TGFβ receptors, or HIF-1α. A nucleotide probe may be labelled with a detectable substance such as a radioactive label which provides for an adequate signal and has sufficient half-life such as $^{32}$P, $^{3}$H, $^{14}$C or the like. Other detectable substances which may be used include antigens that are recognized by a specific labelled antibody, fluorescent compounds, enzymes, antibodies specific for a labelled antigen, and luminescent compounds. An appropriate label may be selected having regard to the rate of hybridization and binding of the probe to the nucleotide to be detected and the amount of nucleotide available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.).

A nucleic acid molecule encoding TGFβ$_3$, TGFβ receptors, or HIF1α can also be detected by selective amplification of the nucleic acid molecules using polymerase chain reaction (PCR) methods. Synthetic oligonucleotide primers can be constructed from the sequences of the TGFβ$_3$, TGFβ receptors, or HIF1α using conventional methods. A nucleic acid can be amplified in a sample using these oligonucleotide primers and standard PCR amplification techniques.

In a preferred embodiment of the invention, a method is provided for diagnosing increased risk of preeclampsia in a subject comprising detecting TGF-β$_3$, TGFβ R-I (ALK-1), TGFβ R-II, endoglin, HIF-1α, or a complex of R-I (ALK-1)-R-II-endoglin in a sample, and in particular using antibodies specific for TGF-β$_3$. Levels of TGF-β$_3$, TGFβ receptors or complexes thereof, or HIF-1α may be measured during the first trimester of pregnancy (approximately 1 to 14 weeks). It is preferred that at least two measurements be taken during this period, preferably including a measurement at about 14 to 16 weeks. If the levels are significantly increased as compared to levels typical for women who do not suffer from preeclampsia, the patient is diagnosed as having an increased risk of suffering preeclampsia. Levels above those typical for women who do not suffer from preeclampsia may be suspect and further monitoring and measurement of $TGF\beta_3$, $TGF\beta$ receptors, or HIF-1α may be appropriate. The information from the diagnostic method may be used to identify subjects who may benefit from a course of treatment, such as treatment via administration of inhibitors of $TGF\beta_3$ as discussed herein.

It will also be appreciated that the above methods may also be useful in the diagnosis or monitoring of choriocarcinoma or hydatiform mole which involves uncontrolled trophoblast invasion (i.e. may be associated with abnormally low levels of $TGF\beta_3$, $TGF\beta$ family receptors, or HIF1α). Further the above methods may be used to diagnose or monitor other pregnancy complications including intrauterine growth restriction, molar pregnancy, preterm labour, preterm birth, fetal anomalies, and placental abruption. The diagnostic and monitoring methods of the invention may also involve determining responsiveness of cells to oxygen.

The invention also relates to kits for carrying out the methods of the invention. The kits comprise instructions, negative and positive controls, and means for direct or indirect measurement of $TGF\beta_3$, $TGF\beta$ receptors, or HIF1α.

2. Regulation of Trophoblast Invasion in a Subject

The invention also provides a method of regulating trophoblast invasion comprising directly or indirectly inhibiting or stimulating (a) $TGF\beta_3$ (b) receptors of cytokines of the $TGF\beta$ family, (c) HIF1α; and/or (d) $O_2$ tension, preferably inhibiting or stimulating $TGF-\beta_3$. Trophoblast invasion may also be regulated by optimizing oxygenation of tissues.

In an embodiment of the invention, a method is provided for increasing trophoblast invasion in a subject comprising administering an effective amount of a substance which is an inhibitor of (a) $TGF-\beta_3$, (b) receptors of cytokines of the $TGF\beta$ family, and/or (c) HIF-1α. In particular, methods are provided for treating a women suffering from or who may be susceptible to preeclampsia.

In another embodiment of the invention, a method is providing for reducing trophoblast invasion in a subject comprising administering an effective amount of (a) $TGF\beta_3$; (b) receptors of cytokines of the $TGF\beta$ family; (c) HIF-α1; and/or (d) a stimulator of (a), (b) or (c). The method may be used to monitor or treat choriocarcinoma or hydatiform mole.

The methods of the invention may also be used to monitor or treat other complications of pregnancy such as intrauterine growth restriction, molar pregnancy, preterm labour, preterm birth, fetal anomalies, or placental abruption.

Substances that regulate trophoblast invasion can be selected by assaying for a substance that inhibits or stimulates the activity of $TGF-\beta_3$, $TGF\beta$ receptors, or HIF-1α. A substance that regulates trophoblast invasion can also be identified based on its ability to specifically interfere or stimulate the interaction of (a) $TGF-\beta_3$ and a receptor for the cytokine (e.g. the interaction of $TGF\beta_3$ and endoglin, or $TGF-\beta_3$ and R-I, R-II, or a complex of R-I-R-II endoglin, or (b) $TGF-\beta_3$ and HIF1α.

Therefore, a method is provided for evaluating a compound for its ability to regulate trophoblast invasion comprising the steps of:

(a) reacting $TGF\beta_3$ or a part thereof that binds to a receptor of a cytokine of the $TGF\beta$ family, with a receptor of a cytokine of the $TGF\beta$ family or a part thereof that binds to $TGF\beta_3$, and a test substance, wherein the $TGF\beta_3$ and receptor of a cytokine of the $TGF\beta$ family or parts thereof, are selected so that they bind to form a ligand-receptor complex; and (b) comparing to a control in the absence of the substance to determine the effect of the substance.

In particular, a method is provided for identifying a substance which regulates trophoblast invasion comprising the steps of:

(a) reacting $TGF\beta_3$ or a part thereof that binds to a receptor of a cytokine of the $TGF\beta$ family, and a receptor of a cytokine of the $TGF\beta$ family or a part thereof that binds to $TGF\beta_3$, and a test substance, wherein the $TGF\beta_3$ and receptor of a cytokine of the $TGF\beta$ family or parts thereof, are selected so that they bind to form a ligand-receptor complex, under conditions which permit the formation of ligand-receptor complexes, and (b) assaying for complexes, for free substance, for non-complexed $TGF\beta_3$ or receptor, or for activation of the receptor.

The substance may stimulate or inhibit the interaction of $TGF\beta$ or a part thereof that binds the $TGF\beta$ receptor, and the $TGF\beta$ receptor.

In an embodiment of the invention a receptor complex is employed comprising $TGF\beta$ R-I (ALK-1)-$TGF\beta$ RII-endoglin.

Activation of the receptor may be assayed by measuring phosphorylation of the receptor, or by assaying for a biological affect on a cell, such measuring biochemical markers of trophoblast invasion such as cell proliferation, FN synthesis, integrin expression, up regulation of gelatinase and type IV collagenase expression and activity.

The invention also provides a method for evaluating a substance for its ability to regulate trophoblast invasion comprising the steps of:

(a) reacting $TGF\beta_3$ or a part of $TGF\beta_3$ that binds to HIF-1α, HIP-1α or a part of the protein that binds to $TGF\beta_3$, and a test substance, wherein the $TGF\beta_3$, or part thereof, and HIF-1α or part thereof bind to form a $TGF\beta3$-HIF-1α complex; and (b) comparing to a control in the absence of the substance to determine the effect of the substance.

The substance may stimulate or inhibit the interaction of $TGF\beta_3$ and HIF-1α, or the activation of $TGF\beta$ by HIF-1α and thereby regulate trophoblast invasion.

The substances identified using the methods of the invention include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, F(ab)$_2$, and Fab expression library fragments, and epitope-binding fragments thereof)]. and small organic or inorganic molecules. The substance may be an endogenous physiological compound or it may be a natural or synthetic compound. The substance may be a $TGF\beta$ R-I-$TGF\beta$ R-II-endoglin complex, which competitively inhibits the binding of $TGF\beta_3$ to its natural receptors. The invention contemplates isolated $TGF\beta$ R-I-$TGF\beta$ R-II-endoglin complexes and their use in regulating trophoblast invasion.

The substances may be peptides derived from the binding sites of TGF-$\beta_3$ and a receptor for the cytokine such as endoglin, R-I or R-II, or a complex of R-I-R-II-endoglin; or the binding sites of TGF-$\beta_3$ and HIF1$\alpha$. A peptide derived from a specific binding site may encompass the amino acid sequence of a naturally occurring binding site, any portion of that binding site, or other molecular entity that functions to bind an associated molecule. A peptide derived from such a binding site will interact directly or indirectly with an associated molecule in such a way as to mimic the native binding domain. Such peptides may include competitive inhibitors, enhancers, peptide mimetics, and the like. All of these peptides as well as molecules substantially homologous, complementary or otherwise functionally or structurally equivalent to these peptides may be used for purposes of the present invention.

"Peptide mimetics" are structures which serve as substitutes for peptides in interactions between molecules (See Morgan et al (1989). Ann. Reports Med. Chem. 24:243–252 for a review). Peptide mimetics include synthetic structures which may or may not contain amino acids and/or peptide bonds but retain the structural and functional features of a peptide, or enhancer or inhibitor of the invention. Peptide mimetics also include peptoids, oligopeptoids (Simon et al (1972) Proc. Natl. Aca, Sci USA 89:9367); and peptide libraries containing peptides of a designed length representing all possible sequences of amino acids corresponding to a peptide of the invention.

Peptides may be synthesized by conventional techniques. For example, the peptides may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3–254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, supra, Vol 1, for classical solution synthesis.)

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

A substance that regulates trophoblast invasion may be a molecule which interferes with the transcription and/or translation of TGF$\beta_3$, TGF$\beta$ receptors, or HIF-1$\alpha$. For example, the sequence of a nucleic acid molecule encoding TGF$\beta_3$, TGF$\beta$ receptors (e.g. endoglin, R-I (ALK-I), R-II, or RI-RII-endoglin complex) or fragments thereof, may be inverted relative to its normal presentation for transcription to produce an antisense nucleic acid molecule. An antisense nucleic acid molecule may be constructed using chemical synthesis and enzymatic ligation reactions using procedures known in the art. Examples of antisense molecules for TGF$\beta_3$ are 5'-CCTTTGCAAGTGCATC-3' (SEQ ID NO:1) and 5'-GATGCACTTGCAAAGG-3' (SEQ ID NO:2).

The treatment methods and compositions described herein may use substances that are known inhibitors of TGF$\beta_3$. For example, antibodies to TGF$\beta_3$, the TGF$\beta$ Binding Compounds including decorin, $\alpha$2-macroglobulin, fetuin, and thyroglobulin, or peptides derived from the sites on these compounds that bind to TGF$\beta_3$, or chimeras of these molecules may be employed.

Activin, another member of the TGF$\beta$ receptor family, triggers trophoblast invasion and therefore it may be used to enhance trophoblast invasion in a subject.

The utility of a selected inhibitor or stimulator may be confirmed in experimental model systems. For example, the human villous explant culture system described by Genbacev et al. (21) can be used to confirm the utility of an inhibitor for treatment of preeclampsia.

In a preferred embodiment of the invention a method is provided for treating a woman suffering from, or who may be suspectible to preeclampsia comprising administering therapeutically effective dosages of an inhibitor of TGF-$\beta_3$ or TGF$\beta$ receptors, an inhibitor of HIF-1$\alpha$, or a substance identified in accordance with the methods of the invention. Preferably treatment with the inhibitor begins early in the first trimester, at about 10 to about 16 weeks, and may continue until measured TGF-$\beta_3$ levels, TGF-$\beta$ receptor levels, or HIF-1$\alpha$ levels are within the normal range. Preferably, treatment with the inhibitor or substance is not continued beyond about 30 weeks of gestation. For the purposes of the present invention normal TGF-$\beta_3$ levels, TGF$\beta$ receptor levels, or HIF-1$\alpha$ levels are defined as those levels typical for pregnant women who do not suffer from preeclampsia. Treatment with the inhibitor is discontinued after TGF-$\beta_3$ levels, TGF-$\beta$ receptor levels, and/or HIF-1$\alpha$ levels are within normal range, and before any adverse effects of administration of the inhibitor are observed.

One or more inhibitors or one or more stimulators of TGF$\beta_3$, TGF$\beta$ receptors, or HIF-1$\alpha$, or substances selected in accordance with the methods of the invention including Binding Compounds, may be incorporated into a composition adapted for regulating trophoblast invasion. In an embodiment of the invention, a composition is provided for treating a woman suffering from, or who may be susceptible to preeclampsia, comprising a therapeutically effective amount of an inhibitor of TGF$\beta_3$, TGF$\beta$ receptors, or HIF-1$\alpha$, or substance selected in accordance with the methods of the invention including TGF$\beta$ Binding Compounds, and a carrier, diluent, or excipient.

The compositions of the invention contain at least one inhibitor or stimulator of TGF-$\beta_3$, TGF$\beta$ receptors, or HIF-1$\alpha$, or substance identified in accordance with the methods of the invention, alone or together with other active substances. Such compositions can be for oral, parenteral, or local use. They are therefore in solid or semisolid form, for example pills, tablets, and capsules.

The composition of the invention can be intended for administration to subjects such as humans or animals. The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle, carrier or diluent. Suitable vehicles are described, for example, in Remnington's Pharmaceutical Sciences (Remington's Pharmaceutical Sciences, Mack Publishing Company, Easton, Pa., USA 1985).

The compositions of the invention may be administered together with or prior to administration of other biological factors that have been found to affect trophoblast proliferation. Examples of these factors include IL-11 (Ireland et al Blood 84:267a. 1994), G-CSF, GM-CSF and M-CSF (U.S. Pat. No. 5,580,554 to Keith).

The compositions and other biological factors may be administered through any known means. Systemic administration, such as intravenous or subcutaneous administration is preferred. A therapeutically effective amount of an active ingredient e.g. inhibitor is an amount effective to elicit the desired therapeutic response but insufficient to cause a toxic reaction. The dosage for the compositions is determined by the attending physician taking into account factors such as the condition, body weight, diet of the subject, and the time of administration.

For example, a therapeutically effective dose of an inhibitor, e.g. an amount sufficient to lower levels of $TGF\beta_3$ to normal levels, is about 1 to 200 µg/kg/day. The method of the invention may involve a series of administrations of the composition. Such a series may take place over a period of 7 to about 21 days and one or more series may be administered. The composition may be administered initially at the low end of the dosage range and the dose will be increased incrementally over a preselected time course.

An inhibitor or stimulator of $TGF\beta_3$, receptors of cytokines of the TGFβ family, or HIF-1α, or substance identified in accordance with the methods of the invention may be administered by gene therapy techniques using genetically modified trophoblasts or by directly introducing genes encoding the inhibitors or stimulators of $TGF\beta_3$, or receptors of cytokines of the TGFβ family, or substances into trophoblasts in vivo. Trophoblasts may be transformed or transfected with a recombinant vector (e.g. retroviral vectors, adenoviral vectors and DNA virus vectors). Genes encoding inhibitors or stimulators, or substances may be introduced into cells of a subject in vivo using physical techniques such as microinjection and electroporation or chemical methods such as coprecipitation and incorporation of DNA into liposomes. Antisense molecules may also be introduced in vivo using these conventional methods.

The following non-limiting examples are illustrative of the present invention:

EXAMPLE 1

Materials and Methods

Establishment of Human Trophoblast Villous Explant Culture

Villous explant cultures were established from first trimester human placentae by a modification of the method of Genbacev et al. (21). First trimester human placentae (5–8 weeks gestation) were obtained from elective terminations of pregnancies by dilatation and curettage. Placental tissue was placed in ice-cold phosphate buffered saline (PBS) and processed within two hours of collection. The tissue was washed in sterile PBS, and aseptically dissected using a microscope to remove endometria tissue and fetal membranes. Small fragments of placental villi (15–20 mg wet weight) were teased apart and placed on a transparent Biopore membrane of 12-mm diameter Millicell-CM culture dish inserts with a pore size of 0.4 µm (Millipore Corp. Bedford, Mass.). The inserts were precoted with 0.2 ml of undiluted Matrigel (Collaborative Research Inc), polymerized at 37° C. for 30 min. and transferred in a 24-well culture dish. Explants were cultured in DMEM/F12 (Gibco, Grand Island, N.Y.) supplemented with 100 µg/ml streptomycin. 100 U/ml penicillin and 0.25 µg/ml ascorbic acid, pH 7.4. Culture media were changed every 48 h and collected for measurement of human chorionic gonadotropin (hCG) and progesterone. Villous explants were kept in culture for up to 6 days. Flattening of the distal end of the villous tips, their adherence to Matrigel and the appearance of extravillous trophoblast cells (EVT) breaking through from the tips, were used as markers of morphological integrity and trophoblast differentiation as previously described by Genbacev et al. (21). EVT cell outgrowth and migration were consistently monitored and quantitated using the ratio of EVT outgrowths/villous tip, where the nominator, EVT outgrowths, represents the number of extravillous trophoblast columns sprouting from the villous tips plus the number of islands of EVT invading into the Matrigel. The denominator represents the total number of villous tips in a single explant culture. EVT outgrowth from the distal end of the villous tips and their migration into the surrounding matrix were observed for up to 6 days in culture.

Initial experiments, in the presence of 10% (v/v) fetal bovine serum (FES), demonstrated that DMEM/F12 supported greater EVT sprouting and migration than DMEM. In order to study the effect of various agents on EVT differentiation, a serum-free villous explant culture system was developed. Villous explants of 5–8 weeks gestation were incubated overnight in DMEM/F12 or DMEM/F12+ 10% (v/v) FBS to promote attachment of the distal villous tips to the Matrigel. Following this incubation period, explants were washed with fresh medium and cultured in either serum-free DMEM/F12 or DMEM/F12 supplemented with varying concentrations of FBS (0.5% and 10%). In serum-free medium EVT/villous tip was 1.58±0.08 while it was 1.32±0.17 in 0.5% FBS and 1.26±0.02 in 10% FBS (mean±s.e.m. of 3 separate experiments, each carried out in triplicate), suggesting that villous explant cultures were viable for at least 6 days in a serum-free medium. All subsequent experiments were performed with DMEM/F12 in the absence of serum.

The viability of the explant cultures was assessed by measuring hCG and progesterone production rate in the culture media collected at the time of media change every 48 h. Both hCG and progesterone concentrations were measured by radioimmunoassays (Coat-A-Count HCG IRMA and progesterone; DPC, Los Angeles, Calif.). Results are expressed for progesterone as ng/0.1 g wet weight tissue and for hCG as IU/0.1 g wet weight tissue.

Antibodies

Murine monoclonal antibody (MAb) 44G4 specific for human endoglin was produced as previously described (22). IgG purified from ascites was used in all functional assays. Rat MAb 7D3 against cytokeratin was a gift from Drs. S. Fisher and C. Damsky (San Francisco, Calif., USA). Murine MAb TS2/7 against the $\alpha_1$ integrin subunit was provided by Dr. M. Hemler (Boston, Mass., USA). Mouse MAb P1D6 against the $\alpha_5$ integrin subunit was from Chemicon (Temecula, Calif.); rat MAb GoH3 against the $\alpha_6$ integrin subunit was purchased from Serotec Canada (Toronto, Ont, Canada) and the neutralizing rabbit polyclonal antibody to TGF-β was from R&D (Minneapolis, Minn.). Purified mouse IgG from Coulter (Hialeah, Fla.) and rat IgG from Sigma (Diagnostic, Toronto, Ont, Canada) were used as negative controls.

Immunohistochemistry

Villous explants kept in culture for 6 days in the presence or absence of antisense oligonucleotides to endoglin were dissected away from the insert membrane with the supporting Matrigel. Explants and placental tissue of 9 weeks gestation were fixed for 1 h at 4° C. in 4% (vol/vol) paraformaldehyde, cryoprotected by incubation in 10% (vol/vol) glycerol for 30 min and 50% (vol/vol) OCT compound (Tissue Tek, Miles, Ind.) for 18 h. embedded in 100% OCT and frozen in liquid nitrogen. Ten micron sections were cut with a cryostat and mounted on poly-L-lysine coated slides. To verify the quality of the tissue and select the most representative sections, every tenth one was stained with haematoxylin and eosin; neighbouring sections were selected and stained using the avidin-biotin immunoperoxidase method. Endogenous peroxidase enzyme activity was quenched with 3% (vol/vol) hydrogen peroxide in 0.01 M Tris-HCl, pH 7.4, containing 0.15 M NaCl, or methanol for 10 minutes. Non-specific binding sites were blocked using 5% (vol/vol) normal horse serum (NHS) and 1% (wt/vol) BSA in Tris-buffer for 40 min at 23° C. In the case of murine monoclonal antibodies, a higher background was observed and it was necessary to preincubate the sections with 5% (wt/vol) texas red-conjugated goat anti-mouse IgG antibody for 1 h at 23° C. prior to incubation with primary antibody at 4° C. for 1 h. Optimal antibody concentrations were established in preliminary experiments by titration and were used as follows: 44G4, 5 µg/ml; rabbit anti-TGF-β, 20 µg/ml; P1D6, 20 µg/ml; GoH3, 0.5 µg/ml; TS2/7, 20 µg/ml; 7D3, 10 µg/ml. The slides were washed three times with Tris-buffer, then incubated with a 200-fold dilution of biotinylated goat anti-rabbit IgG or a 300-fold dilution of biotinylated horse anti-mouse or anti-rat IgG, for 1 h at 4° C. After washing three times with Tris-buffer, the slides were incubated with an avidin-biotin complex for 1 h. Slides were washed again in Tris-buffer and developed in 0.075% (wt/vol) 3,3-diaminobenzidine in Tris-buffer, pH 7.6, containing 0.002% (vol/vol) $H_2O_2$ giving rise to a brown product. After light counterstaining with toluidine blue, slides were dehydrated in an ascending ethanol series, cleared in xylene, and mounted. In control experiments, primary antibodies were replaced with non-immune mouse or rat IgG, or blocking solution [5% (vol/vol) NGS and 1% (wt/vol) BSA].

Effect of Antibody to Endoglin on EVT Formation

Villous explants, prepared from placentae of 5–8 weeks gestation, were incubated for 16 h in DMEM/F12. Explant cultures were then washed with fresh serum-free medium and incubated in serum-free DMEM/F12 medium containing increasing concentrations of MAb 44G4 IgG (0.1 to 10 µg/ml). DMEM/F12 medium±antibody was replaced every 48 h. Antibody addition was thus performed on day 1, 3 and 5 of culture. Morphological integrity of villous explants and their EVT differentiation were monitored daily for up to 6 days.

Antisense Oligonucleotides and Their Effects on EVT Formation

Phosphorothioate oligonucleotides (ON) were synthesized on a DNA synthesizer and purified by capillary electrophoresis. Oligonucleotides of 16 base pairs targeted against sequences adjacent to the AUG initiation codon of human endoglin (23) mRNA were synthesized. Previous studies have demonstrated that antisense oligonucleotides, targeted to sequences adjacent to initiation codons, are most efficient in inhibiting translation (24). Furthermore, 16-mer oligonucleotides are short enough to be taken up efficiently and provide sufficient specificity for hybridization to the corresponding target mRNA (24). The sequences of the antisense and sense endoglin oligonucleotides were 5'-GCGTGCCGCGGTCCAT-3' (SEQ ID NO:3) and 5'-ATGGACCGCGGCACGC-3' (SEQ ID NO:4), respectively. An oligomer with the same composition as the antisense oligonucleotide, but with a scrambled sequence, 5'-GCGGGCCTCGTTCCAG-3' (SEQ ID NO:5), was also synthesized and used as a negative control. Oligonucleotides were dissolved in water and their concentration was estimated by optical density at $OD_{260}$. Antisense or sense oligonucleotides (5–10 µM) were added to the villous explants on day 1 and day 3 of culture. EVT sprouting and migration from the distal end of the villous tips were recorded daily for up to 6 days.

Villous explants of 5–8 weeks gestation were incubated overnight in DMEM/F12. Explants were then washed and incubated in DMEM/F12 containing either 10 µg/ml MAb 44G4 or non-immune IgG, 10 µM antisense, scrambled or sense endoglin oligonucleotides. The medium with or without the various agents was changed on day 3 and was replaced on day 5 by methionine-cysteine free low glucose DMEM containing 25 µCi/ml of [$^{35}$S]methionine/cysteine with or without the same antibodies or oligonucleotides. The cultures were metabolically labelled for 18 h. Conditioned culture media were collected and diluted with an equal amount of 25 mM Tris-HCl buffer, pH 7.4, 0.15 M NaCl and 0.5% (v/v) Triton X-100 and fibronectin was isolated using gelatin-Sepharose as previously described (25). Briefly, 50 µl of the gelatin-Sepharose suspension was added to 500 µl of medium and the samples were incubated overnight at 4° C. The gelatin-Sepharose beads were centrifuged, washed three times in Tris/Triton X-100 buffer and fibronectin was eluted by boiling for 5 min in 1% (v/v) SDS and electrophoresed on a 4–12% (w/v) polyacrylamide gradient gels. Radiolabeled fibronectin was revealed by autoradiography and quantitated using a PhosphoImager (410A and Image Quant software, Molecular Dynamics).

[$^3$H]Thymidine Incorporation into DNA

Villous explants of 5–8 weeks gestation, cultured for 48 h with and without antisense ON to endoglin, were incubated in the presence of 1 µCi of [$^3$H]thymidine per milliliter of medium. After 6 h of incubation explants were washed with PBS, fixed in 4% paraformaldehyde for 1 h, embedded in OCT and processed for cryostat sections as previously described. Ten micron sections were mounted on 3-aminopropyl-tryethoxysilane-precoated slides and coated with NBT-2 emulsion (Eastman Kodak, Rochester, N.Y.). Slides were developed after 3 days using Kodak D-19 developer, counterstained with eosin and examined by bright-field microscopy.

Data Analysis

All data are presented as means±s.e.m. of at least three separate experiments carried out in triplicate. Statistical significance was determined by Student's (t)-test for paired groups and by one-way analysis of variance followed by assessment of differences using Student-Newman-Keuls test for non-paired groups. Significance was defined as p<0.05.

Results

Stimulation of EVT Outgrowth and Migration by Antibody and Antisense Oligonucleotides to Endoglin The morphological examination of villous explants of 5–8 weeks gestation, cultured in serum-free medium, revealed a pattern of EVT differentiation (cell outgrowth and migration) similar to that described by Genbacev et al (21). The viability of the explants, as measured by the rate of production of progesterone and hCG, remained relatively constant for up to 6 days.

The ability of an antibody to endoglin (MAb 44G4) to alter the early events of EVT differentiation along the invasive pathway was examined. Exposure of villous explants of 5–8 weeks gestation to 44G4 IgG was associated with an increase in EVT outgrowth from the distal end of the villous tips and a higher number of cells migrating into the surrounding matrix. Stimulation of EVT outgrowth and migration by 44G4 IgG was specific as incubation of explants with an equivalent amount of non-immune murine IgG or medium alone had no effect. Furthermore addition of 44D7 IgG (10 µg/ml) reactive with CD98 antigen expressed at high levels on syncyuotrophoblast (26) had no stimulatory effect.

Antisense endoglin also enhanced the number of EVT outgrowths as well as their migration and invasion into the Matrigel. Control explants, cultured in the presence of sense endoglin oligonucleotides, exhibited no such effect.

Further experiments demonstrated that 24 h after the addition of 44G4 IgG (day 2 of culture) there was a significant increase in EVT outgrowth and migration from 0.20±0.03 in the control group to 2.03±0.46 in the antibody treated group (n=4; p<0.005). After 5 days of treatment (day 6) the number of EVT outgrowths increased from 0.64±0.09 in control IgG-treated explants to 3.2±0.5 in the 44G4 IgG-treated explants (n=10, p<0.05). Subsequent experiments demonstrated that the stimulatory effect of 44G4 IgG was dose-dependent and maximal at 1 µg/ml.

The stimulatory effect of antisense endoglin oligonucleotides on EVT outgrowth and migration was observed on day 3 of culture with 6.87±1.5 in the antisense-treated group versus 1.42±0.41 in the sense-treated group (p<0.05). After 5 days of exposure, the number of EVT/villous tip increased from 2.08±0.47 in sense-treated explants to 8.46±1.7 in antisense-treated cultures. The antisense-endoglin effect on trophoblast differentiation was specific as incubation of explants with an equivalent amount of either sense endoglin or scrambled antisense-endoglin oligonucleotide (not shown) had no effect. Antisense endoglin stimulated EVT outgrowth and migration in a concentration-dependent manner with maximal stimulation observed at 10 µM.

Characterization of Trophoblast Differentiation Along the Invasive Pathway in Villous Explants Culture Previous reports indicate that stem trophoblasts within the villous core and at the proximal site of the column, where trophoblasts start to migrate away from the stem villi, undergo proliferation (21), whereas differentiated EVT do not. Therefore, studies were carried out to determine if EVT outgrowth triggered by antisense endoglin treatment was due to cell division or migration. [$^3$H]Thymidine autoradiography of explants exposed to antisense endoglin ON showed villous trophoblast proliferation within the villous tip at the proximal site of the forming column, while both differentiated EVT, which have invaded the surrounding Matrigel, and mesenchymal cells in the villous core did not show any DNA synthesis. This suggests that EVT within the column do not divide and that blockage of endoglin most likely induces cell migration from the villous core.

Trophoblast differentiation in situ is accompanied by a temporally and spatially regulated switch in integrin repertoire (4). When placental explants of 5–8 weeks gestation were maintained in culture for 5 days in the presence of antisense-endoglin oligonucleotides, the stimulation of EVT outgrowth and migration was also accompanied by changes in integrin expression. The $\alpha_6$ integrin subunit was found on polarized cytotrophoblasts within the villi and on the non-polarized trophoblasts in the proximal columns. The $\alpha_5$ integrin subunit was minimally expressed on polarized trophoblasts or syncytium, but was present on EVT within the columns. EVT which had migrated further away in the Matrigel were negative for the $\alpha_5$ integrin. All trophoblast cells, including CTB within the villi, the syncytiotrophoblast and EVT stained positively for cytokeratin confirming the epithelial-like nature of the cells forming the columns and migrating into the Matrigel. EVT which have migrated into Matrigel were positive for the $\alpha_1$ integrin. A polygonal antibody to TGF-β showed staining of the syncytiotrophoblast and stroma of the villi, suggesting that TGF-β was present in the culture system. Migrating EVT and the Matrigel itself, known to contain TGF-β, showed weak positive staining. No reactivity was observed in the explants stained with control IgG.

As little EVT outgrowth is observed under basal culture conditions, the expression of endoglin in trophoblast columns could only be studied in antisense-treated explants. Immunohistochemical analysis of explants treated with antisense oligonucleotides to endoglin revealed that in intact villi the syncytiophoblast maintained high levels of endoglin. Low levels of endoglin and $\alpha_5$ integrin were observed in the stroma; however this staining appears non-specific as it was also observed with non-immune IgG. The staining of endoglin in EVT of explants treated with antisense endoglin was weakly positive when compared to sections of the same explant stained with control IgG. In addition, endoglin expression in proximal columns of explants was much reduced when compared to sections of 9 weeks gestation placenta stained under similar conditions. When a subsequent section of this placenta is stained for $\alpha_5$ integrin, the transition zone in the proximal column is clearly visualized as negative for $\alpha_5$, but positive for endoglin. The $\alpha_5$ integrin in explants treated with antisense endoglin was also found to be highly expressed in EVT within proximal and distal columns. These data suggest that antisense endoglin treatment, which promotes EVT outgrowth and migration in explant cultures, induces a decrease in endoglin expression at the level of the transition zone, which is followed by an increase in the expression of the $\alpha_5$ integrin fibronectin receptor.

Stimulation of Fibronectin Production by Interference with TGF-β Response

FN has been more localized to specific regions of the matrix surrounding the anchoring villi and its production is increased during EVT differentiation (27). Thus the effect of either 44G4 IgG or antisense endoglin on fibronectin synthesis by villous explants from 5–8 weeks gestation was investigated. Explants were metabolically labelled on day 4 with [$^{35}$S]methionine and newly synthesized FN released into the media over a period of 18 h was measured. Both 44G4 IgG and antisense-endoglin oligonucleotides induced a significantly greater production of FN than that observed in control IgG or sense oligonucleotide-treated cultures. PhosphoImager analysis of all data demonstrated a 8- and 5-fold increase in FN synthesis (5 independent experiments carried out in triplicate, p<0.05) for 44G4 IgG and antisense-endoglin treated explants, respectively, relative to control sense or DMEM/F12 alone. FN production in villous explants, cultured in the presence of a scrambled antisense endoglin oligonucleotide, was similar to that observed in sense-treated explants or in medium alone.

To demonstrate that endoglin is an essential component of the receptor complex in mediating the effects of TGF-$β_1$ and TGF-$β_3$, villous explants were preincubated with either antisense or antibody to endoglin to trigger EVT differentiation. After an overnight incubation, exogenous TGF-$β_1$, TGF-$β_2$ or TGF-$β_3$ were added at a concentration of 10 ng/ml. Explants were metabolically labelled at day 5 of culture and FN synthesis was measured. PhosphoImager analysis demonstrated that both antibody and antisense to endoglin significantly stimulated FN synthesis. Addition of exogenous TGF-$\beta_1$ and TGF-$\beta_3$ to explant cultures incubated with antisense ON or antibody to endoglin, which binds both isoforms, did not alter the stimulatory effect of antisense ON and antibody to endoglin on FN synthesis. In contrast, addition of TGF-$\beta_2$, which does not interact with endoglin, overcame the antibody and antisense ON stimulatory effect on FN synthesis. TGF-$\beta_2$, but not -$\beta_1$ and -$\beta_3$, inhibited also the EVT outgrowth and migration induced by the antisense endoglin treatment.

Discussion

Treatment of human villous explants from 5–8 weeks gestation with antibodies and antisense oligonucleotides to endoglin stimulated EVT differentiation along the invasive pathway. This was manifested by 1) a significant increase in EVT outgrowth and migration, 2) an increase in fibronectin production 3) stem villous trophoblast proliferation and 4) a switch in integrin expression similar to that observed in vivo during formation of anchoring villi. These data suggest that endoglin regulates EVT differentiation during placental development. Endoglin, which is expressed in vivo in the transition area where polarized trophoblasts break through the syncytium and begin forming columns of non-polarized cells, appears to be a key molecule in mediating the inhibition of trophoblast differentiation.

During the first trimester of gestation TGF-$\beta$ is colocalized with one of its natural inhibitors, decorin, in the ECM of decidual tissue, suggesting that this proteoglycan may aid TGF-$\beta$ storage or limit its activity within the decidual ECM (12). The findings described herein suggest that TGF-$\beta$ produced by the villi is a negative regulator of trophoblast differentiation along the invasive pathway. The expression of endoglin at the transitional zone from polarized to non-polarized trophoblasts appears essential to the mediation of this negative regulation. Blocking endoglin expression in this transition phase triggers EVT outgrowth and migration and FN production. Thus, trophoblast invasion, characteristic of normal human placentation, is dependent on an intricate balance between positive and negative regulators. The data herein indicate that endoglin is a critical negative regulator of this system. Therefore, inappropriate expression or function of endoglin may contribute to the major complications of pregnancy such as preeclampsia or choriocarcinoma, associated with abnormal trophoblast invasion and placenta development.

EXAMPLE 2

The present experiments were conducted to define the precise components that endogenously regulate trophoblast invasion. Using human villous explants of 5–7 weeks gestation it was observed that while trophoblast cells remain viable they do not spontaneously invade into the surrounding matrigel. In contrast, trophoblast cells from 9–13 weeks explants spontaneously invade the matrigel in association with an upregulation of fibronectin synthesis and integrin switching. Trophoblast invasion at 5–7 weeks can be induced by incubation with antisense to TGF-$\beta_3$, TGF$\beta$ receptor I (ALK-1) or TGF$\beta$ receptor II. Only minimal invasion occurred in response to antisense to TGF$\beta_1$ and antisense TGF$\beta_2$ failed to induce invasion. These data suggest that TGF-$\beta_3$ via the ALK-1-receptor II complex is a major regulator of trophoblast invasion in vitro. To determine whether this system may also operate in vivo, immunohistochemical staining was conducted for TGF-$\beta$1 and -3 and for TGF$\beta$ receptor I and II in trophoblast tissue from 5–13 weeks of gestation. Strong positive immunoreactivity was observed for TGF-$\beta_3$ in both cyto- and syncytiotrophoblast from 5–9 weeks of gestation but immunoreactivity was markedly reduced by 12–13 weeks. Expression of TGF$\beta_1$ was absent at 5 weeks, and transiently expressed at around 8 weeks of gestation. TGF receptor I and II immunoreactivity was strong between 5–8 weeks but was not present at 12–13 weeks. Thus, the presence of TGF$\beta_3$ and its receptors at 5–8 weeks at a time when there is no spontaneous trophoblast invasion in vitro and the absence of these molecules at 12–13 weeks when spontaneous in vitro invasion occurs is consistent with a major role for TGF-$\beta_3$ as an endogenous inhibitor of trophoblast invasion.

EXAMPLE 3

Studies were carried out to determine if shallow trophoblast invasion in preeclampsia was associated with an abnormally sustained inhibition of invasion by TGF-$\beta$. In particular, the expression/distribution of the different TGF-$\beta$ isoforms and their receptors was investigated using immunohistochemical analysis in normal placentae at 7–9 weeks (at the onset of trophoblast invasion) at 12–13 weeks (the period of peak invasion), in control placentae between 29 and 34 weeks and in preeclamptic placentae ranging from 27 to 34 weeks. In normal placentae, TGF-$\beta_3$ expression was markedly reduced with advancing gestational age. Expression was high in cyto- and syncytiotrophoblast cells at 7–9 weeks of gestation but was absent in villous tissue at 12–13 weeks and at 29–34 weeks of gestation. A similar decline in positive immunoreactivity against TGF-$\beta$ receptor I and II was also observed over this time period. In contrast, in preeclamptic placentae between 27–34 weeks of gestation, strong staining for TGF-$\beta_3$ and its receptors was present in syncytiotrophoblast and stromal cells, immunopositive reactivity was not detected against TGF-$\beta_1$ or TGF-$\beta_2$ in either normal or preeclamptic placentae. These data indicates that preeclampsia may result from a failure of trophoblast cells to downregulate expression of TGF-$\beta_3$ and its receptors which continue to exert an inhibitory influence on trophoblast invasion into the uterine wall.

EXAMPLE 4

Materials and Methods

RT-PCR and Southern Blot Analysis

Total RNA was extracted from the placenta, reverse transcribed and amplified by 15 cycles of PCR using TGF$\beta$ isoform specific primers. RT-PCR products were analysed by Southern blotting using $^{32}$P-labelled TGF$\beta$ cDNAs. The primer set chosen for amplification of TGF$\beta$s were based on human mRNA sequences. Primers used for amplification were: (a) TGF$\beta_1$ cNDA: (forward primer): 5'-GCCCTGGACACCAACTATTGCT-3' (SEQ ID NO:6), (reversed primer): 5'-AGGCTCCAAATGTAGGGGC AGG-3' (SEQ ID NO:7) (predicted product size=161 bp); (b) TGF$\beta_2$ cDNA (forward primer): 5'-CATCTGGTCCCGGTGGCGCT-3' (SEQ ID NO:8), (reversed primer): 5'-GACGATTCTGAAGTAGGG-3' (SEQ ID NO:9) (predicted product size=353 bp; (c) TGF$\beta_3$ cDNA: (forward primer): 5'-CAAAGGGCTCTGGTGGTCCTG-3' (SEQ ID NO:10), (reversed primer): 5'-CTTAGAGGTAATTCCCTTGGGG-3' (SEQ ID NO:11) (predicted product size=374 bp); (c) $\beta$-actin cDNA: forward primer): 5'-CTTCTACAATGAGCTGGGTG-3' (SEQ ID NO:12), (reversed primer): 5'-TCATGAGGTAGTCAGTCAGG-3' (SEQ ID NO:13) (predicted product size=307 bp). The identity of the PCR reaction products was also confirmed by sequencing.

Immunohistochemistry

Placental tissue was processed for immunocytochemistry as previously described (I. Caniggia et al Endocrinology, 138, 3976 1997). Purified rabbit polyclonal antibody directed against TGFβ$_1$, TGFβ$_2$ and TGFβ$_3$ (Santa Cruz Biotechnology, Santa Cruz, Calif.) were used at 1:50 dilution. Sections (7 μm) were stained using the avidin-biotin immunoperoxidase method (I. Caniggia et al *Endocrinology*, 138, 3976 1997). Control experiments included replacement of primary antibodies with antiserum preincubated with an excess of TGFβs (competing peptide) or with blocking solution [5% (vol/vol) NGS and 1% (wt/vol) BSA].

Human Villus Explant Culture System

Villous explant cultures were established as described previously (I. Caniggia et al. *Endocrinology*, 138, 3976 1997, O. Genbacev et al., Placenta 13:439, 1992) from first trimester human placentae (5–10 weeks gestation) or from preeclamptic and age-matched control placentae (30 and 32 weeks of gestation) after collection according to ethical guidelines. The preeclamptic group was selected according to both clinical and pathological criteria (L. Chesley, *Obstet. Gynecol.* 65, 423, 1985). Following an overnight period in serum-free DMEM/F12, explants were cultured in media containing antisense or sense oligonucleotides (10 μM) for up to 6 days (with changes of media/oligonucleotides every 48 hours). Phosphorothioate oligonucleotides of 16 base pairs targeted against sequences adjacent to the AUG initiation codon of different human TGFβ isoforms mRNA were synthesized as follows: TGFβ$_1$ 5'-CCCCGAGGGCGGCATG-3' (SEQ ID NO:14) and 5'-CATGCCGCCCTCGGGG-3' (SEQ ID NO:15), respectively; TGFβ$_2$ 5'-CACACAGTAGTGCATG-3' (SEQ ID NO:16) and 5'-CATGCACTACTGTGTG-3' (SEQ ID NO:17); TGFβ$_3$ 5'-CCTTTGCAAGTGCATC-3' (SEQ ID NO:18) and 5'-GATGCACTTGCAAAGG-3' (SEQ ID NO:19).

Fibronectin Synthesis

To measure fibronectin synthesis on day 5 explants were cultured in the presence of 25 μCi/ml of [$^{35}$S]methionine/cysteine for 18 hours. Conditioned culture media were collected and diluted with an equal amount of 25 mM Tris-HCl buffer, pH 7.4, 0.15 M NaCl and 0.5% (v/v) Triton X-100 and fibronectin was isolated using gelatin-Sepharose as previously described (I. Caniggia et al *Endocrinology*, 138, 3976 1997, E. Engvall et al *Int. J. Cancer,* 20: 1, 1977). Radiolabeled fibronectin was revealed by autoradiography and quantitated using a PhosphoImager (410A and Image Quant software, Molecular Dynamics).

Gelatinolytic Activity

Analysis of gelatinolytic activity was performed using 10% polyacrylamide gel (wt/vol) impregnated with 0.1% gelatin (NOVEX, San Diego, Calif.) as previously described (I. Caniggia et al *Endocrinology*, 138, 3976 1997). For Western blot analysis of metalloproteases expression, 5 μl of conditioned media were subjected to gel electrophoresis using 10% polyacrylamide gels. Proteins were then blotted to Westran PVDF membrane. Primary antibodies were used at 1:100 dilution, and detected using horse radish peroxidase conjugated antimouse IgG (Amerham 1:10,000 fold dilution) and enhanced by chemiluminescence (ECL, Amerham).

Results

The expression of TGFβ around 9–12 weeks of pregnancy and its relationship to trophoblast invasion and subsequently preeclampsia were investigated. Using low cycle RT-PCR followed by Southern blot analysis all three isoforms of TGFβ were found to be expressed during the first trimester (FIG. 3A). However, while transcripts corresponding to TGFβ$_1$ and TGFβ$_2$ were uniformly expressed throughout this period, the expression of TGFβ$_3$ exhibited a striking pattern of developmental or temporal regulation. TGFβ$_3$ mRNA levels were relatively low at 5–6 weeks, increased markedly between 7 and 8 weeks, and then fell precipitously at 9 weeks. This pattern of expression for the TGFβ$_3$ isoform was confirmed at the protein level by immunohistochemistry (FIG. 3B). TGFβ$_3$ was localized to cyto and syncytiotrophoblasts within the villous and also to cytotrophoblasts within the invading column (FIG. 3B). TGFβ$_3$ was noticeably absent in those cytotrophoblast cells at the transition between polarized and non-polarized cells at the proximal site of the forming column. Importantly, the down-regulation of TGFβ$_3$ around 9 weeks is temporally associated with the period of maximal trophoblast invasion in vivo and the expression of markers of cytotrophoblast invasion, including switching of integrin isoforms (Damsky, C. H. et al Development 120:3657, 1994), synthesis of matrix ligands for these integrins (P. Bischof, L. Haenggeli A. Campana, *Human Reprod.* 10, 734, (1995), M. J. Kupfermine, A. M. Peaceman, T. R. Wigton, K. A. Rehnberg, M. A. Socol, *Am.J. Obstet. Gynecol.* 172, 649 (1995)) and upregulation of gelatinase A (MMP2) and gelatinase B (MMP9) activity (C. I. Librach, et al. *J.Biol. Chem.* 269, 17125, (1994)).

Figure 4A:
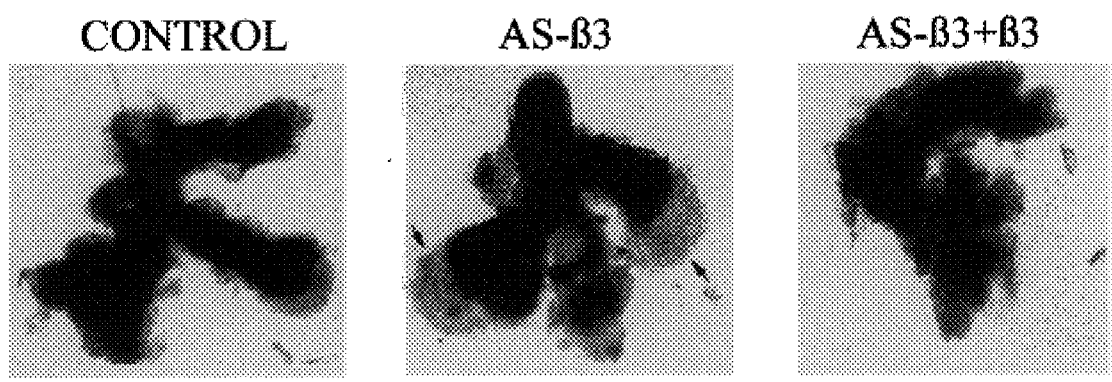
FIG. 4A are photographs showing that addition of recombinant TGF$\beta_3$ to antisense TGF$\beta_3$ abolishes the antisense stimulatory effect on trophoblast budding and outgrowth.
Figure 4B:
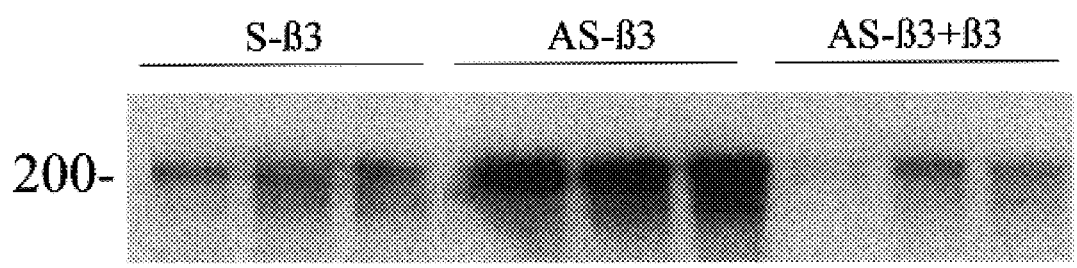
FIG. 4B are blots showing the reversal effect on antisense TGF$\beta_3$ stimulatory effect by exogenous TGF$\beta_3$ for fibronectin synthesis.
Figure 4C:
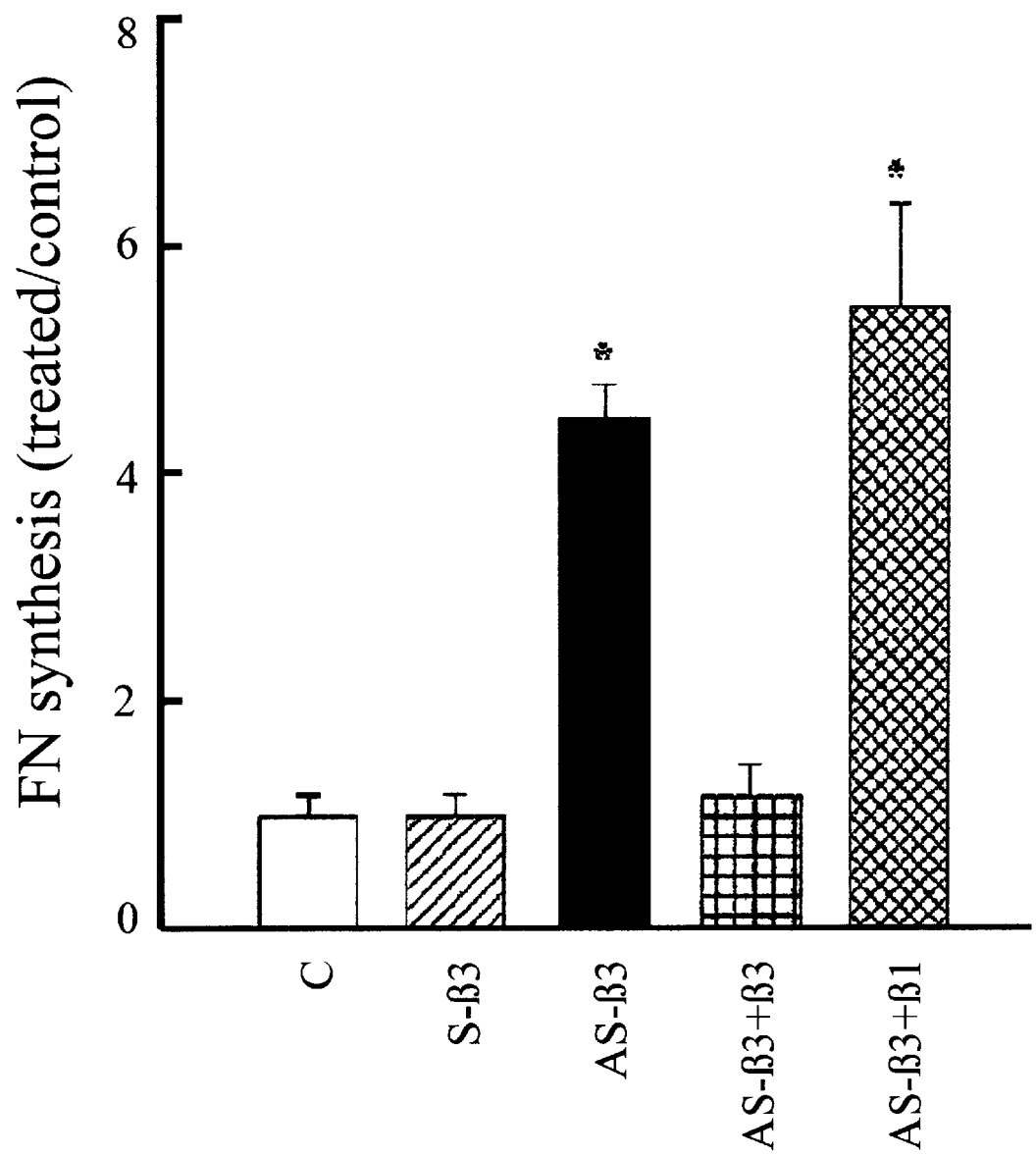
FIG. 4C is a graph showing the changes in fibronectin estimated after normalization to control cultures.
Figure 4D:
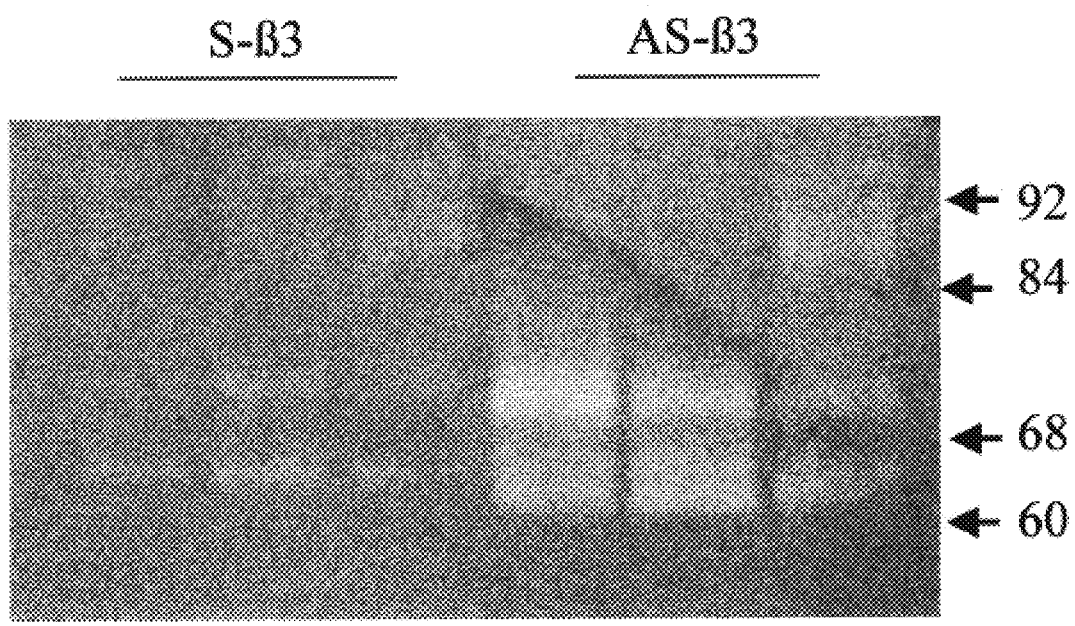
FIG. 4D are blots showing the effects on gelatinase activity in conditioned media of explants treated with sense or antisense oligonucleotides to TGF$\beta_3$.
Figure 4E:
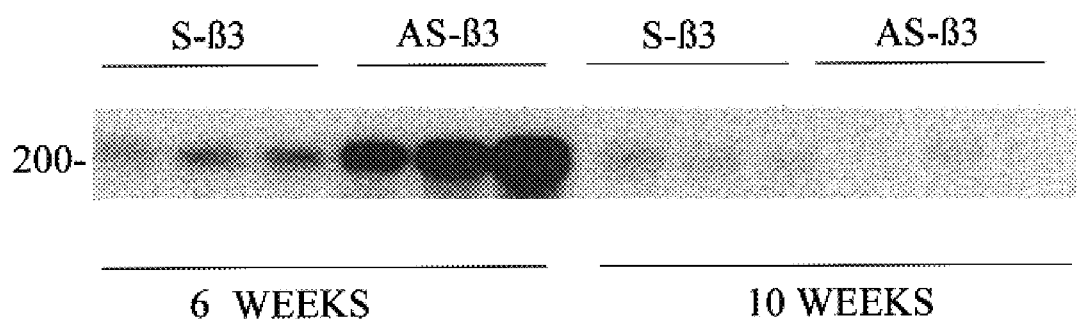
FIG. 4E are blots showing that the antisense TGF$\beta_3$ stimulatory effect on fibronectin production is lost after 9 weeks of gestation.

To determine the functional significance of the TGFβ expression patterns, a human villus explant culture system was used which mimics closely the normal pattern of trophoblast invasion in vivo (I. Caniggia, C. V. Taylor, J. W. K. Ritchie, S. J. Lye, M. Letarte, *Endocrinology*, 138, 4977 (1997), O. Genbacev, S. A. Schubach, R. K. Miller, *Placenta* 13, 439, (1992)). Morphologic (EVT outgrowth) and biochemical (fibronectin [FN] synthesis and gelatinase activity) indices of trophoblast invasion were monitored in response to antisense (AS) induced suppression of TGFβ isoform expression in explants at 5–8 weeks of gestation. Explants exposed to AS TGFβ$_3$ (but not TGFβ$_1$ or TGFβ$_2$) displayed prominent EVT outgrowth from the distal end of the villous tip (FIG. 4A). This morphologic response was associated with a significant increase in FN synthesis (FIG. 4B, and FIG. 4E) and gelatinase activity (FIG. 4D). The specificity of the AS TGFβ$_3$ response was demonstrated by reversal of both morphologic and biochemical indices when AS-treated explants were cultured in the presence of TGFβ$_3$ but not TGFβ$_1$ (FIG. 4C). The induction of FN synthesis by AS TGFβ$_3$ at 5–8 weeks was lost at 9–13 weeks (FIG. 4E) further demonstrating the specificity of the AS action as TGFβ$_3$ is not expressed in villous trophoblast at 9–12 weeks.

Figure 5A:
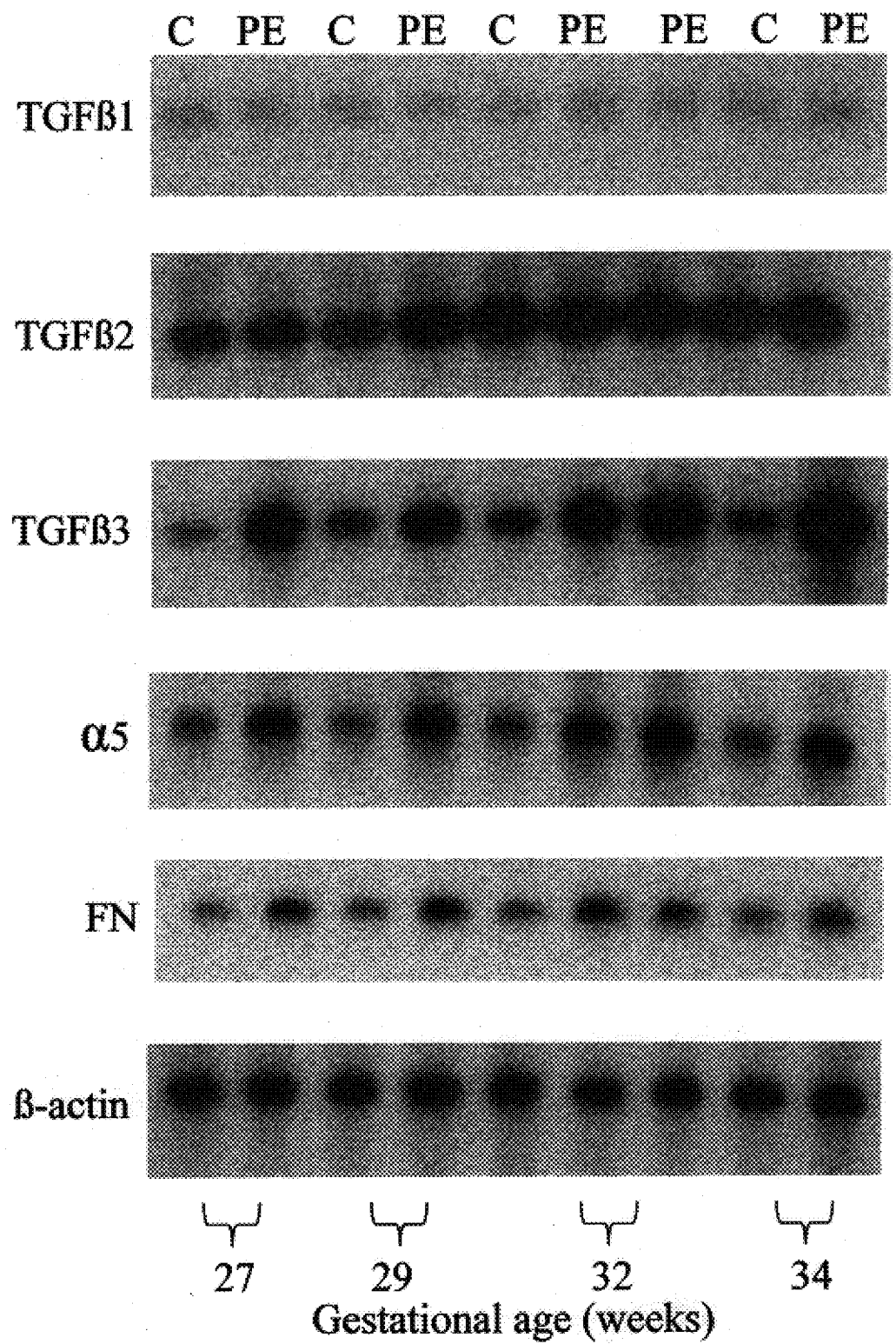
FIG. 5A are blots showing message expression of TGF$\beta$ isoforms, $\alpha_5$ integrin receptor, and fibronectin in preeclamptic and age-matched control placentae.
Figure 5B:
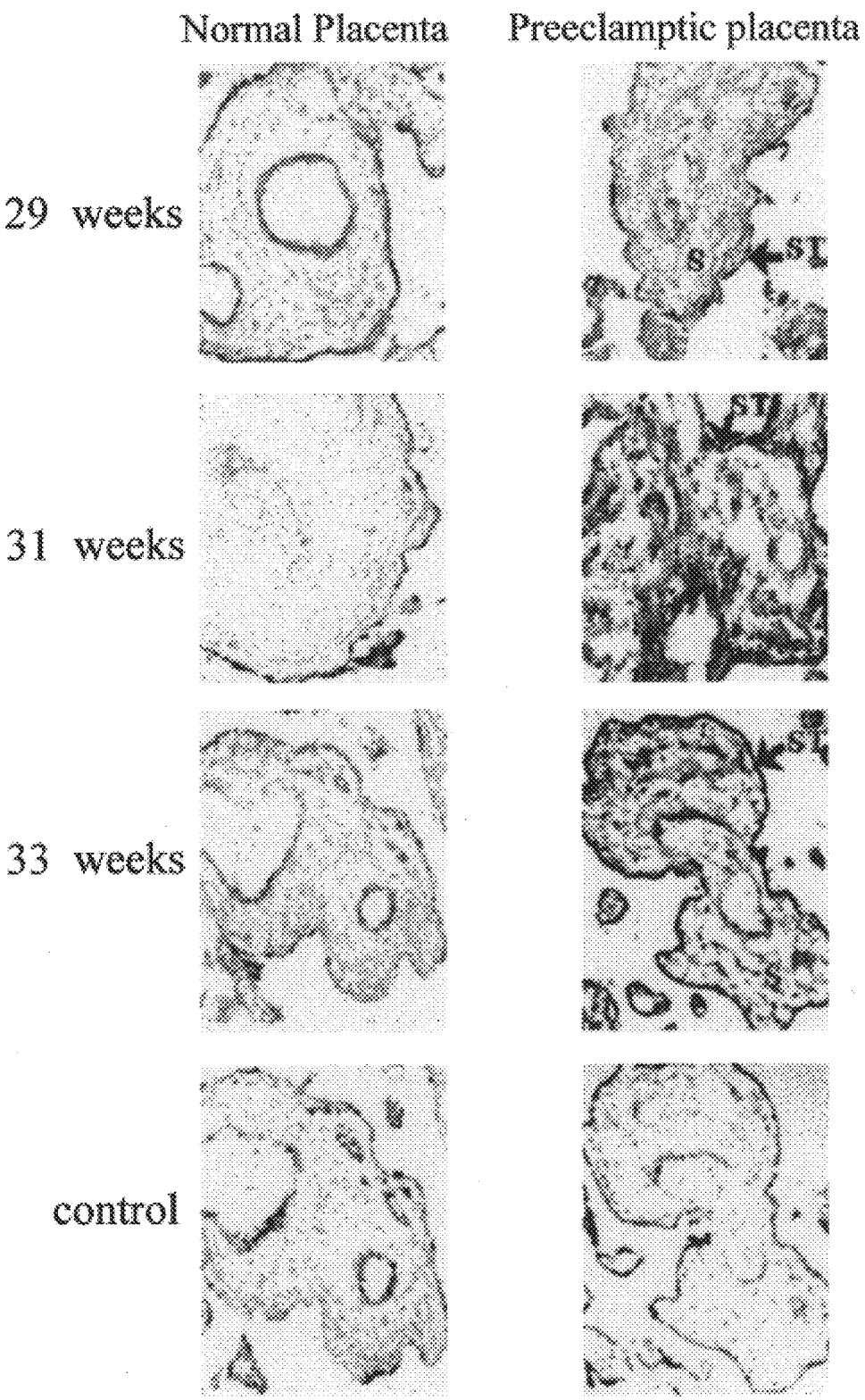
FIG. 5B are photographs of immunoperoxidase staining of TGF$\beta_3$ performed in placental sections from normal pregnancies and pregnancies complicated by preeclampsia.

These functional data together with the temporal-spatial expression patterns strongly suggest that down-regulation of TGFβ$_3$ around 9–12 weeks is required for optimal trophoblast invasion indicate that a failure to down-regulate TGFβ$_3$ expression is the basis of limited trophoblast invasion found in preeclampsia. Significantly higher levels of mRNA encoding TGFβ$_3$ (but not TGFβ$_1$ or TGFβ$_2$) were found in preeclamptic versus control placentae (FIG. 5A). Immunoreactive TGFβ$_3$ intensively labelled syncytio and cytotrophoblasts in villous tissues from preeclamptic patients while little or no immunoreactivity was present in the age-matched controls (FIG. 5B). Elevated levels of FN mRNA and a failure to complete integrin switching (i.e the trophoblast remain positive for α$_5$ and fail to express α$_1$ were also obverved in preeclamptic placentae. These data suggest that the trophoblasts from preeclamptic placenta are arrested at a relatively immature phenotype possibly due to a failure to undergo complete differentiation along the invasive pathway during the first trimester of gestation.

Figure 6A:
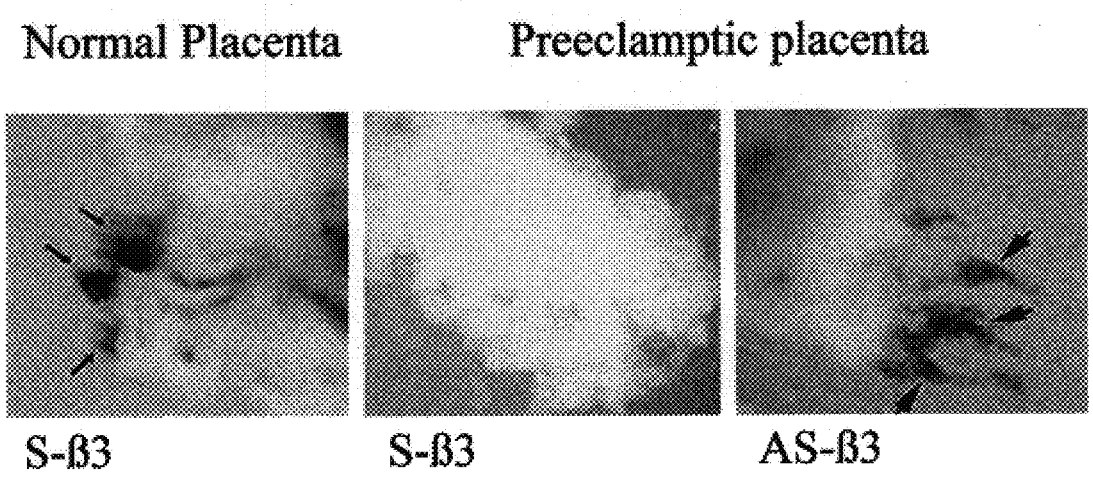
FIG. 6A are photographs showing that antisense oligonucleotides to TGF$\beta_3$ induces the formation of trophoblast cells in preeclamptic villous explants.
Figure 6B:
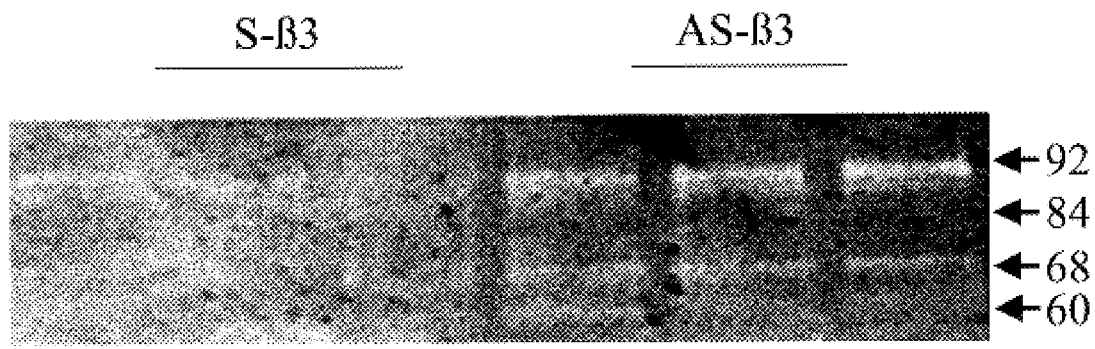
FIG. 6B shows the results of gelatin Zymography of explants of 32 weeks gestation from preeclamptic placentae treated with antisense or control sense oligonucleotides to TGFβ$_3$ for 5 days.
Figure 6C:
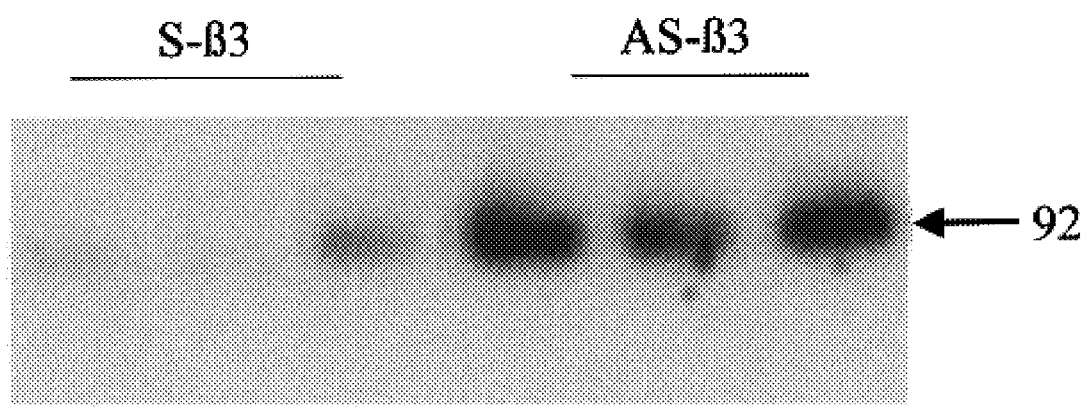
FIG. 6C are Western blots with MMP9 antisera of explants of 32 weeks gestation from preeclamptic placentae treated with antisense or control sense oligonucleotides to TGFβ$_3$ for 5 days.

To determine whether there was functional significance associated with overexpression of $TGF\beta_3$ in preeclamptic placentae, the pattern of trophoblast differentiation along the invasive pathway in explants from control and preeclamptic patients was analyzed. When cultured on matrigel, explants from non-preeclamptic patients showed formation of EVT columns which spontaneously invaded into the surrounding matrigel. In contrast, explants from preeclamptic placentae failed to exhibit EVT outgrowth or invasion (FIG. 6A). These data are consistent with the view that preeclampsia is associated with reduced invasive capability of trophoblasts. Of critical importance to the investigation was whether this reduced invasive capability was due to the overexpression of $TGF\beta_3$. Therefore the differentiation of villous explants from preeclamptic patients cultured in the presence of AS $TGF\beta_3$ was monitored. In contrast to untreated or sense-treated controls, treatment of explants from preeclamptic patients with AS $TGF\beta_3$ restored the invasive capability, as demonstrated by the formation of EVT columns migrating through the matrigel (FIG. 6A). The invasive nature of this phenotype was confirmed by the finding that explants treated with AS $TGF\beta_3$ acquired the expression of gelatinase B/MMP9, an enzyme which is normally only expressed in trophoblast cells that are highly invasive (FIG. 6B and FIG. 6C).

The data presented here demonstrate not only that abnormalities in $TGF\beta_3$ expression are associated with preeclampsia but also that down-regulation of $TGF\beta_3$ with antisense oligonucleotides restores the invasive capability of preeclamptic trophoblasts. The data are consistent with a model of normal placentation in which down-regulation of $TGF\beta_3$ expression in trophoblast around 9 weeks of pregnancy permits differentiation of trophoblast to EVT that form the anchoring villi and from which derive the α1-integrin positive EVT which invade deep into the maternal uterus. This invasion contributes to the remodelling of the uterine spiral arteries and ultimately enables the establishment of increased vascular perfusion of the placenta. In placentae predisposed to preeclampsia, $TGF\beta_3$ expression remains abnormally elevated and trophoblasts remain in a relatively immature state of differentiation. As a direct consequence, trophoblast invasion into the uterus is limited and uteroplacental perfusion is reduced. This conclusion is consistent with the clinical manifestations of preeclampsia, including shallow trophoblast invasion into the uterus and abnormally high uteroplacental vascular resistance.

EXAMPLE 5
Role of $O_2$ Tension in Trophoblast Invasion

Figure 7A:
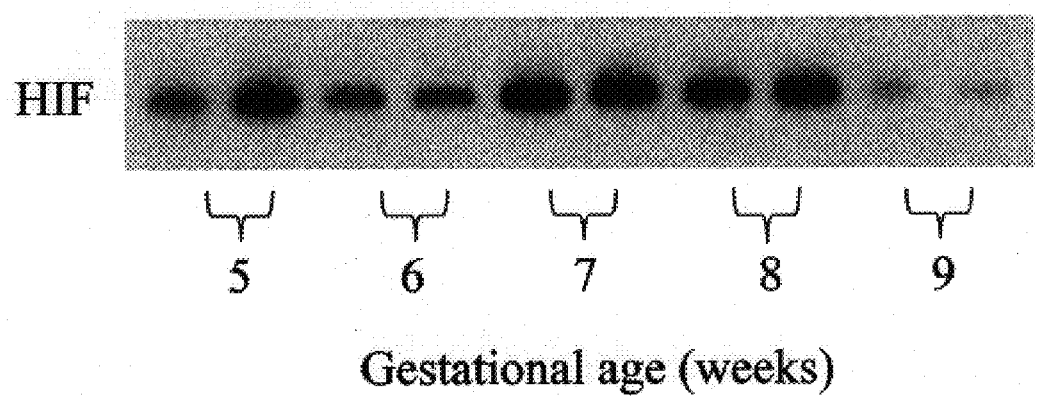
FIG. 7A is a blot showing expression of HIF-1α placenta in the first trimester of gestation.
Figure 7B:
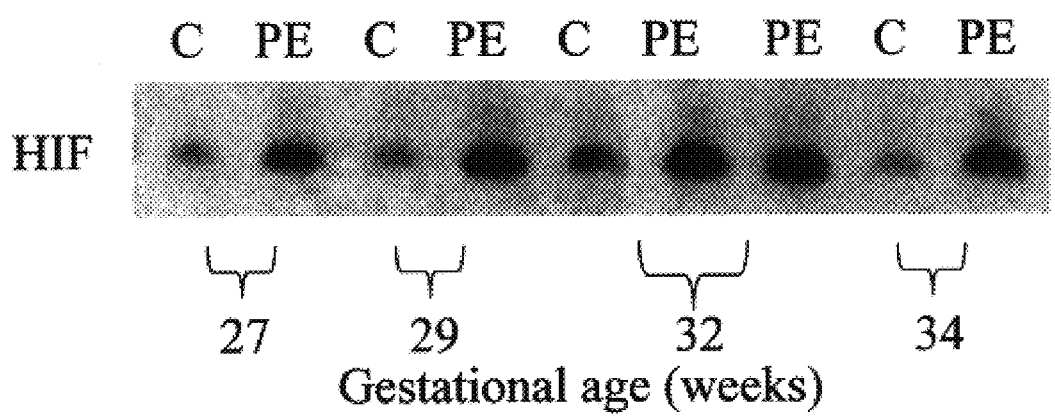
FIG. 7B is a blot showing expression of HIF-1α in preeclamptic (PE) and age-matched control placenta (C)
Figure 8:
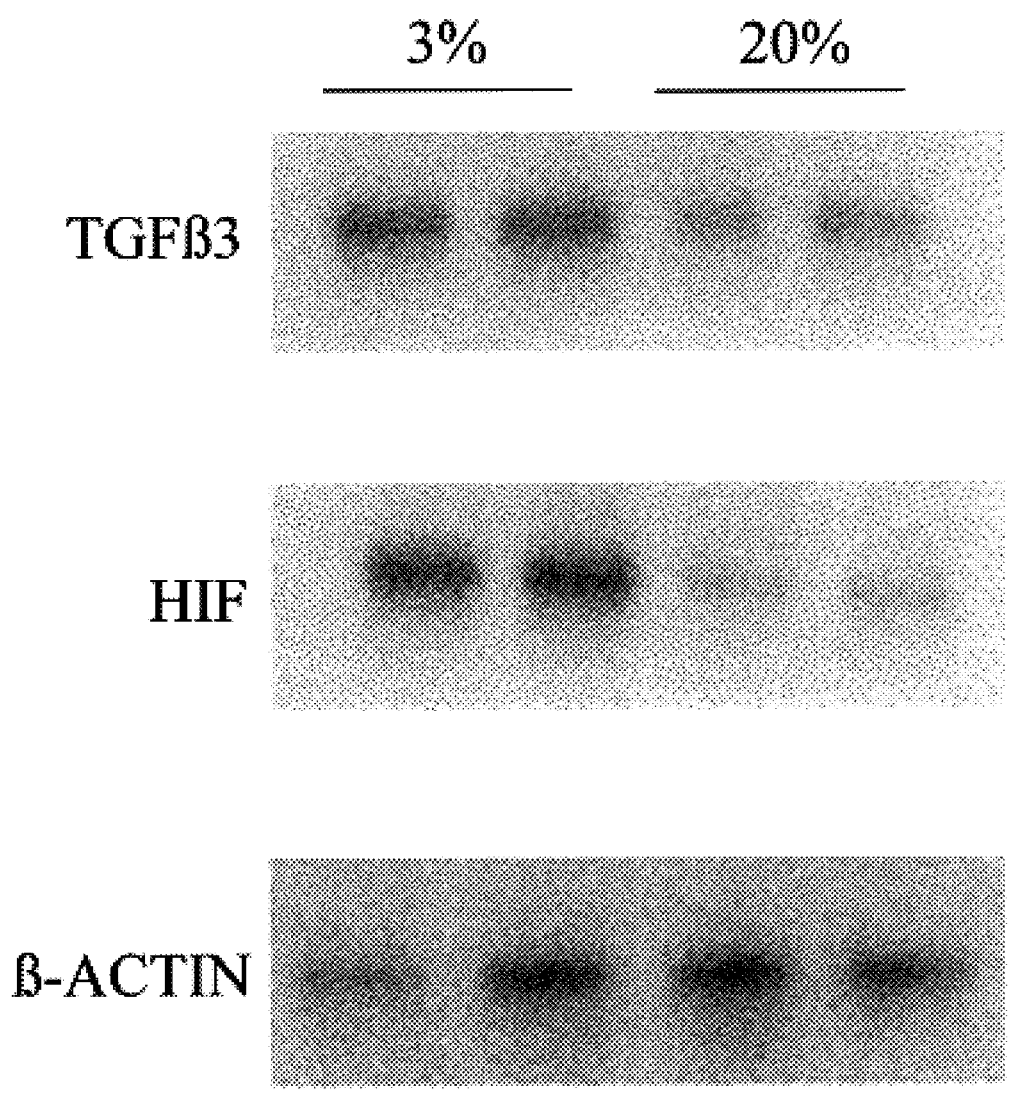
FIG. 8 is a blot showing the effect of low oxygen tension on TGFβ$_3$ and HIF-1α expression in villous explants.

The role of oxygen tension in regulating trophoblast differentiation along the invasive pathway has been investigated. The data indicate that expression of hypoxia inducible factor HIF-1α parallels that of $TGF\beta_3$ in first trimester trophoblast (i.e. peaks at 6–8 weeks but deceases after 9–10 weeks when oxygen tension increases (FIG. 7A). The presence of putative HIF-1 binding sites in the promoter region of the $TGF\beta_3$ gene suggests that induction of HIF-1α by low $PO_2$ (around 6–8 weeks) up regulates $TGF\beta_3$ transcription and blocks a trophoblast invasion. A failure of the system to down-regulate at 9–12 weeks (either due to a block in response to normoxia or the absence of an increase in oxygen tension) could lead to shallow invasion and predispose to preeclampsia. This is supported by data showing that expression of HIF-1α is dramatically increased in placentas of preeclamptic patients when compared to age-matched control tissue (FIG. 7B). In FIGS. 7A and 7B mRNA HIF-1α expression was assessed by using low cycle RT-PCR followed by Southern blot analysis. This is also supported by FIG. 8 showing the effect of low oxygen tension of $TGF\beta_3$ and HIF-1α expression in villous explants; FIG. 9 showing the effect of low oxygen tension on villous explant morphology; and FIG. 10 showing the effect of antisense to HIF-1α on villous explant morphology.

EXAMPLE 6
$TGF\beta_3$ Signals Through a Receptor Complex

In addition to endoglin, evidence indicates that $TGF\beta_3$ signals through a receptor complex which includes RI (ALK-1) and RII. While TGFβ R-I (ALK-5) and TGFβ R-II are expressed throughout the villi and decidua at 9–10 weeks gestation; they are absent from the base of the proximal columns of the anchoring villi at the transition zone between the villous and the invading EVT, exactly at the site where endoglin is upregulated. This dramatic change in TGF-β receptor expression suggests that EVTs within the columns in situ are not subject to the inhibitory actions of TGFβ but via R-I and R-II they do come under the control of this ligand upon entering the decidua. The potential clinical importance of the TGFβ receptor system in trophoblast invasion is highlighted by data demonstrating that beside $TGF\beta_3$, R-I is expressed at greater levels in trophoblast tissue of preeclamptic patients when compared to that in age-matched control placenta. Antisense disruption of R-I (ALK-1) and R-II expression stimulated trophoblast outgrowth/migration and FN synthesis. In contrast, antisense to R-I (ALK-5) inhibited FN synthesis.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Below full citations are set out for the references referred to in the specification and detailed legends for the figures are provided.

FULL CITATIONS FOR REFERENCES REFERRED TO IN THE SPECIFICATION

1. Cross J C, Werb Z, Fisher, S J, 1994. Implantation and the placenta: key pieces of the development puzzle. Science, 266:1508–1518.
2. Zhou Y, Damsky C H, Chiu K, Roberts J M, Fisher S J, 1993. Preeclampsia is associated with abnormal expression of adhesion molecules by invasive cytotrophoblasts. J. Clin. Invest. 91: 950–960.
3. Aplin J D, 1991. Implantation, trophoblast differentiation and haemochorial placentation: mechanistic evidence in vivo and in vitro. J. Cell Science, 99: 681–692.
4. Damsky C H, Fitzgerald M L, Fisher S J, 1992. Distribution patterns of extracellular matrix components and adhesion receptors are intricately modulated during first trimester cytotrophoblast differentiation along the invasive pathway, in vivo. J. Clin. Invest. 89: 210–222.
5. Bischof P, Redard M, Gindre P, Vassilakos P, Campana A, 1993. Localization of alpha2, alpha5 and alpha6 integrin subunits in human endometrium, decidua and trophoblast. Eur. J. of Obst. and Gyn. and Repr. Biol. 51: 217–226.

6. St-Jacques S, Forte M, Lye S J, Letarte M, 1994. Localization of endoglin, a transforming growth-factor-b binding protein, and of CD44 and integrins in placenta during the first trimester of pregnancy. Biol Reprod. 51: 405–413.
7. Fisher S J, Cui T, Zhang L et al. 1989. Adhesive and degradative properties of human placental cytotrophoblast cell in vitro. J. Cell. Biol. 109: 891–902.
8. Librach C L, Feigenbaun S L, Bass K E, et al. 1994. Interleukin-1b regulates human cytotrophoblast metalloprotenase activity and invasion in vitro. J. Biol. Chem. 269: 17125–17131.
9. Bass K E, Morrish D, Roth I, et al. 1994 Human cytotrophoblast invasion is up-regulated by epidermal growth factor: evidence that paracrine factors modify this process. Devel. Biol. 164: 550–561.
10. Graham C H, Lysiak J J, McCrae K R, Lala P K, 1992. Localization of transforming growth factor-b at the human fetal-maternal interface: role in trophoblast growth and differentiation.
Biol. Reprod. 46: 561–572.
11. Graham C H, Lala P K, 1991. Mechanism of control of trophoblast invasion in situ. J. Cell. Physiol. 148: 228–234.
12. Lysiak J J, Hunt J, Pringle J A, Lala P K, 1995. Localization of transforming growth factor b and its natural inhibitor decorin in the human placenta and decidua throughout gestation. Placenta, 16: 221–231.
13. Irving J A, and Lala P K, 1995. Functional role of cell surface integrins on human trophoblast cell migration: regulation by TGF-b, IGF-II, and IGBP-1. Exp. Cell. Res. 217: 419–427.
14. Cheifetz S, Bellon T, Cales C, et al. 1992. Endoglin is a component of the transforming growth factor-b receptor system in human endothelial cells. J. Biol. Chem. 267: 19027–19030.
15. Wrana J L, Attisano L, Wieser R, Ventura F, Massague J, 1994. Mechanisms of activation of the TGF-b receptor. Nature, 370: 341–347.
16. Mitchell E J, Fitz-Gibbon L, O'Connor-McCourt M D, 1992. Subtypes of betaglycan and type I and type II transforming growth factor-b (TGF-b) receptors with different affinities for TGF-b1 and TGF-b2 are exhibited by human placenta trophoblasts. J. Cell. Physiol. 150: 334–343.
17. Gougos A, St-Jacques S, Greaves A, et al. 1992. Identification of distinct epitopes of endoglin, an RGD-containing glycoprotein of endothelial cells, leukemic cells, and syncytiotrophoblasts. Int. Immunol. 4: 83–92.
18. Yamashita H, Ichijo H, Grimsby S, Moren A, ten Dijke P, and Miyazono K, 1994. Endoglin forms an heteromeric complex with the signalling receptors for transforming growth factor-b. J. Biol. Chem. 269: 1995–2001.
19. Zhang H, Shaw A R E, Mak A, and Letarte M, 1996. Endoglin is a component of the TGF-b receptor complex of human pre-B leukemic cells. J. Immunol. 156: 565–573.
20. Lastres P, Letamendia A, Zhang H, et al. 1996. Endoglin modulates cellular responses to TGF-b1. J. Cell Biol. 133: 1109–1121.
21. Genbacev O, Schubach S A, Miller R K, (1992). Villous culture of first trimester human placenta-Model to study extravillous trophoblast (EVT) differentiation. Placenta, 13: 439–461.
22. Quackenbush E J and Letarte M, 1985. Identification of several cell surface proteins of non-T, non-B acute lymphoblastic leukemia by using monoclonal antibodies. J. Immunol. 134: 1276–1285.
23. Gougos A, and Letarte M, 1990. Primary structure of endoglin, an RGD-containing glycoprotein of human endothelial cells. J. Biol. Chem. 265: 8361–8364.
24. Malcolm A D B, 1992. Uses and applications of anti-sense oligonucleotides: uses of antisense nucleic acids-an introduction. Bioch. Soc. Trans. 20: 745–746.
25. Engvall E, and Ruoslahti E, 1977. Binding of soluble form of fibroblast surface protein, fibronectin, to collagen. Int. J. Cancer, 20: 1–5.
26. Soubiran P, Hsi B-L, Lipinski M, Yeh C-J G, Vaigot P, Masseyeff R, 1986. Distribution of Trop 3 and 4 antigens as defined by monoclonal antibodies raised against a human choriocarcinoma cell line. A.J.R.I.M. 12: 118–123.
27. Feinberg R F, Kilman H J, Locwood C J, 1991 Is oncofetal fibronectin a trophoblast glue for human implantation? Am. J. Pathol. 138: 537–543.
28. Vicovac I, Jones C J, Aplin J D, 1995. Trophoblast differentiation during formation of anchoring villi in a model of the early human placenta in vitro. Placenta, 16: 41–56.
29. Feinberg R F, Kliman H J, Wang C-L, 1994. Transforming growth factor-b stimulates trophoblast oncofetal fibronectin synthesis in vitro: implications for trophoblast implantation in vivo. J.Clin. Endocrinol Metab. 78: 1241–1248.
30. Bischof P, Haenggeli L, and Campana A, 1995. Gelatinase and oncofetal fibronectin secretion is dependent on integrin expression on human cytotrophoblasts. Molecular Human Reproduction, 10: 734–742.
31. Damsky C H, Librach C, Lim K-H, et al. 1994. Integrin switching regulates normal trophoblast invasion. Development, 120: 3657–3666.

DETAILED FIGURE LEGENDS

FIG. 3

Expression of TGF-$\beta$ isoforms in human placenta in the first trimester of gestation. (FIG. 3A) Message expression of TGF$\beta$ isoforms was assessed by low cycle RT-PCR followed by Southern blot analysis using specific probes for TGF$\beta_1$, TGF$\beta_2$ and TGF$\beta_3$ and the control house-keeping gene $\beta$-actin. Note that TGF$\beta_3$ expression increases around 7–8 weeks gestation and declines thereafter. (FIG. 3B) Immunoperoxidase staining of TGF$\beta_3$ was performed in placental sections at 5, 8 and 12 weeks of gestation. Sections of placental tissue of 5 weeks gestation show positive immunoreactivity visualized by brown staining in the cytotrophoblast, syncytiotrophoblast and stromal cells of the chorionic villi. Sections of placental tissue of 8 weeks gestation show strong positive immunoreactivity in the cytotrophoblast, syncytiotrophoblast, and stromal cells. Note that TGF-$\beta_3$ was expressed in the non-polarized trophoblast within the column (EVT, thin arrow) but was absent in the transitional zone where polarized cells become unpolarized (thick arrows). Sections of placenta at 12 weeks gestation demonstrate low or absent TGF-$\beta_3$ immunoreactivity in the villi. There is no immunoreactivity when antiserum was preincubated with an excess of TGF$\beta_3$ competing peptide (8 weeks, control).

FIG. 4

Antisense TGF$\beta_3$ stimulates trophoblast migration, fibronectin production and gelatinase, activity. Explants of 5–8 weeks gestation were treated for 5 days with 10 $\mu$M antisense oligonucleotides to TGF$\beta_3$ (AS-$\beta$3), AS-$\beta$3 plus 10 ng/ml recombinant TGF$\beta_3$ (AS-$\beta$3+$\beta$3) or AS-$\beta$3 plus recombinant TGF$\beta$1 (AS-$\beta$3+$\beta$1). Control experiments were run in parallel using sense TGF-$\beta_3$ (S-$\beta$3) or medium alone (FIG. 4C). (FIG. 4A) Shown is a representative experiment demonstrating that addition of recombinant TGFβ$_3$ to antisense TGFβ$_3$ treated explants (AS-β3+β3) abolishes the antisense stimulatory effect on trophoblasts budding and outgrowth (arrows). (FIG. 4B) Similar reversal effect on AS-β3 stimulatory effect by exogenous TGFβ$_3$ was demonstrated also for fibronectin synthesis. Representative analysis of triplicate samples from a single experiments is shown. The position of the marker with $M_r=200\times10^3$ is indicated. Lanes 1–3, S-β3 treated explants; lanes 4–6. AS-β3 treated explants; lanes 7–9, AS-β3+β3 treated explants. (FIG. 4C) Changes in fibronectin estimated after normalization to control cultures. Antisense TGFβ$_3$ treatment (AS-β3, solid bar) significantly incresed (p<0.05; one-way ANOVA followed by Student-Newman-Keuls test for non-paired groups) the amount of labelled fibronectin compared to both medium alone (FIG. 4C, open bar) or sense (S-β3, cross bar). Addition of exogenous TGFβ$_3$ (AS-β3+β3 squares bar) but not TGFβ$_1$ (AS-β3+β1 cross hatched bar) to the antisense treated explants abolished the antisense stimulatory effect on fibronectin production, demonstrating the specificity of the action of TGFβ$_3$. (FIG. 4D) Getatinase activity in conditioned media of explants treated with sense or antisense oligonucleotides to TGFβ3. Arrows indicate positions of getatinases activity (MMP2: 60, 68; MMP9: 84 and 92, kDa). (FIG. 4E) The antisense TGFβ$_3$ stimulatory effect on fibronectin production is lost after 9 weeks of gestation. Explants of 6 and 10 weeks gestation were treated with 10 µM antisense (AS-β3) or control sense (S-β3) oligonucleotides to TGFβ$_3$. Newly synthesized fibronectin was isolated from the medium as described above. Representative analysis of triplicate samples from a single experiment is shown. Lanes 1–3 and 7–9, S-β3 treated explants; lanes 4–6 and 10–12, AS-β3 treated explants.

FIG. 5

TGFβ$_3$ is overexpressed in preeclamptic placentae. (FIG. 5A) Message expression of TGFβ isoforms, α$_5$ integrin receptor and fibronectin in preeclamptic (PE) and age-matched control placentae (FIG. 5C) was assessed by low cycle RT-PCR followed by Southern blot analysis using specific probes for TGFβ$_1$, TGFβ$_2$, TGFβ$_3$, α$_5$, fibronectin and the control house-keeping gene β-actin. Note that TGFβ$_3$, α$_5$ and fibronectin, but not TGFβ$_1$ or TGFβ$_2$, expression were higher in preeclamptic placentae when compared to age-matched control. (FIG. 5B) Immunoperoxidase staining of TGFβ$_3$ was performed in placental sections from normal pregnancies and pregnancies complicated by preeclampsia. Sections of normal placental tissue of 29, 31 and 33 weeks of gestation show low/absent TGFβ$_3$ immunoreactivity in cells of the chorionic villi. Sections of preeclamptic placental tissue of the same gestation show strong positive immunoreactivity visualized by brown staining in the cytotrophoblast, syncytiotrophoblast and stromal cells of the chorionic villi. Control experiments were performed using antiserum preabsorbed with an excess of peptide.

FIG. 6A

Antisense oligonucleotides to TGFβ$_3$ induces the formation of columns of trophoblast cells in preeclamptic villous explants. Villous explant cultures were prepared from preeclamnptic and age-matched control placentae. Explants were maintained in culture in the presence of either control sense or antisense oligonucleotides to TGFβ$_3$ for 5 days. Morphological integrity was recoded daily. Explants from normal placenta (32 weeks), exposed to sense oligonucleotides (S-β3) spontaneously form columns of trophoblast cells which migrate and invade into the surrounding Matrigel (arrows), while explants from preeclamptic placenta (32 weeks) exposed to sense oligonucleotides do not. In contrast, antisense treatment (AS-β3) triggers the formation of invading trophoblast columns (arrows) in preeclamptic placentae.

FIG. 6B and FIG. 6C

Antisense oligonucleotides to TGFβ$_3$ triggers gelatinase activity and expression in preeclamptic villous explants. Explants of 32 weeks gestation from preeclamptic placentae were treated with antisense (AS-β3) or control sense (S-β3) oligonucleotides to TGFβ$_3$ for 5 days. Samples of conditioned medium were collected at day 5 and subjected to analysis by gelatin Zymography (FIG. 6B) or Western blotting with MMP9 antisera (FIG. 6C). Arrows indicate positions of gelatinases activity (MMP-2: 60, 68; MMP-9: 84 and 92, kDa).

We claim:

1. A method for diagnosing increased risk of preeclampsia in a subject which comprises: (a) measuring levels of placental expression of a TGF-β type I receptor (ALK-I) (RI), endoglin or TGF-β type II receptor (R-II) in a sample from the subject; and (b) comparing the levels of expression of TGF-β type I receptor (ALK-I)(RI), endoglin or TGF-β type II receptor (R-II) to the levels in a woman with normal pregnancy, wherein increased levels of TGF-β type I receptor (ALK-I)(RI), endoglin or TGF-β type II receptor (R-II) compared to levels in a woman with a normal pregnancy indicates an increased risk of preeclampsia in the subject.

2. A method as claimed in claim 1, wherein the levels of placental expression of the TGF-β type I receptor (ALK-I) (RI), endoglin or TGF-β type II receptor (R-II) are measured by detecting, directly or indirectly, the interaction of the TGF-β type I receptor (ALK-I)(RI), endoglin or TGF-β type II receptor (R-II) in the sample with an antibody specific for the TGF-β type I receptor (ALK-I)(RI), endoglin or TGF-β type II receptor (R-II).

3. A method as claimed in claim 2, wherein the antibody is labeled with an enzyme, fluorescent, luminescent or radioactive material.

4. A method as claimed in claim 1, wherein the antibody is used in counter immuno-electrophoresis, a radioimmunoassay, radioimmunoprecipitation assay, an enzyme-linked immuno-sorbent assay (ELISA), a dot blot assay, an inhibition or competition assay or a sandwich assay.

5. A method as claimed in claim 2, wherein the antibody is labeled with a first partner of a ligand binding pair and the TGF-β type I receptor (ALK-I)(RI), endoglin or TGF-β type II receptor (R-II) are coupled to a second partner of a ligand binding pair that binds to the first partner.

6. A method as claimed in claim 1, wherein the levels of placental expression of the TGF-β type I receptor (ALK-I) (RI), endoglin or TGF-β type II receptor (R-II) are measured by detecting nucleic acid sequences encoding the TGF-β type I receptor (ALK-I)(RI), endoglin or TGF-β type II receptor (R-II).

7. A method as claimed in claim 6, wherein the nucleic acid sequences encoding the TGF-β type I receptor (ALK-I)(RI), endoglin or TGF-β type II receptor (R-II) are detected using a nucleotide probe which hybridizes to the nucleic acid sequences.

8. A method as claimed in claim 6, wherein the nucleic acid sequences encoding the TGF-β type I receptor (ALK-I)(RI), endoglin or TGF-β type II receptor (R-II) are detected by selective amplification of the nucleic acid sequences using polymerase chain reaction.

9. A method for diagnosing the increased risk of preeclampsia in a subject comprising: (a) measuring a level of placental expression of $TGF\beta_3$ in a sample from the subject, and (b) comparing the level of $TGF\beta_3$ in the sample to a level of $TGF\beta_3$ in a woman with normal pregnancy, wherein an increased level of $TGF\beta_3$ compared to the level in the woman with normal pregnancy indicates an increased risk of preeclampsia in the subject.

10. A method according to claim 9, wherein the level of placental expression of $TGF\beta_3$ is measured during the first trimester of pregnancy.

11. A method according to claim 9, wherein the level of placental expression of $TGF\beta_3$ is detected directly or indirectly using an antibody specific for $TGF\beta_3$.

12. A method according to claim 11, wherein the antibody is labeled with an enzyme, or a fluorescent, luminescent, or radioactive material.

13. A method according to claim 11, wherein the expression of $TGF\beta_3$ is detected using a counter immuno-electrophoresis, a radioimmunoassay, radioimmunoprecipitation, an enzyme-linked immuno-sorbent assay (ELISA), a dot blot assay, competitive inhibition assay, or a sandwich assay.

14. A method according to claim 9, wherein the level placental expression of $TGF\beta_3$ is measured by detecting nucleic acid sequences encoding $TGF\beta_3$.

15. A method according to claim 14, wherein nucleic acid sequences encoding $TGF\beta_3$ are detected using a nucleotide probe which hybridizes to the nucleic acid sequences.

16. A method according to claim 14, wherein the nucleic acid sequences encoding $TGF\beta_3$ are detected by selective amplification of the nucleic acid sequences using polymerase chain reaction.

* * * * *

UNITED STATES PATENT AND TRADEMARK OFFICE
CERTIFICATE OF CORRECTION

PATENT NO.     : 6,376,199 B1
DATED          : April 23, 2002
INVENTOR(S)    : Caniggia et al.

It is certified that error appears in the above-identified patent and that said Letters Patent is hereby corrected as shown below:

<u>Title page,</u>
Item [73], Assignees, "The Hospital for Sick Children (HSC)" should be deleted so that the only assignees are -- Mount Sinai Hospital Corporation; Martin Post, all of Toronto (CA) --.

Signed and Sealed this

Twenty-fifth Day of November, 2003

JAMES E. ROGAN
*Director of the United States Patent and Trademark Office*

SEQUENCE LISTING

<160> NUMBER OF SEQ ID NOS: 24

<210> SEQ ID NO 1
<211> LENGTH: 16
<212> TYPE: DNA
<213> ORGANISM: Homo sapiens

<400> SEQUENCE: 1
cctttgcaag tgcatc                                           16

<210> SEQ ID NO 2
<211> LENGTH: 16
<212> TYPE: DNA
<213> ORGANISM: Homo sapiens

<400> SEQUENCE: 2
gatgcacttg caaagg                                           16

<210> SEQ ID NO 3
<211> LENGTH: 16

```
<212> TYPE: DNA
<213> ORGANISM: Homo sapiens

<400> SEQUENCE: 3
gcgtgccgcg gtccat                                                          16

<210> SEQ ID NO 4
<211> LENGTH: 16
<212> TYPE: DNA
<213> ORGANISM: Homo sapiens

<400> SEQUENCE: 4
atggaccgcg gcacgc                                                          16

<210> SEQ ID NO 5
<211> LENGTH: 16
<212> TYPE: DNA
<213> ORGANISM: Homo sapiens

<400> SEQUENCE: 5
gcgggcctcg ttccag                                                          16

<210> SEQ ID NO 6
<211> LENGTH: 22
<212> TYPE: DNA
<213> ORGANISM: Homo sapiens

<400> SEQUENCE: 6
gccctggaca ccaactattg ct                                                   22

<210> SEQ ID NO 7
<211> LENGTH: 22
<212> TYPE: DNA
<213> ORGANISM: Homo sapiens

<400> SEQUENCE: 7
aggctccaaa tgtaggggca gg                                                   22

<210> SEQ ID NO 8
<211> LENGTH: 20
<212> TYPE: DNA
<213> ORGANISM: Homo sapiens

<400> SEQUENCE: 8
catctggtcc cggtggcgct                                                      20

<210> SEQ ID NO 9
<211> LENGTH: 18
<212> TYPE: DNA
<213> ORGANISM: Homo sapiens

<400> SEQUENCE: 9
gacgattctg aagtaggg                                                        18

<210> SEQ ID NO 10
<211> LENGTH: 21
<212> TYPE: DNA
<213> ORGANISM: Homo sapiens

<400> SEQUENCE: 10
caaagggctc tggtggtcct g                                                    21
```

<210> SEQ ID NO 11
<211> LENGTH: 22
<212> TYPE: DNA
<213> ORGANISM: Homo sapiens

<400> SEQUENCE: 11
cttagaggta attcccttgg gg                                              22

<210> SEQ ID NO 12
<211> LENGTH: 20
<212> TYPE: DNA
<213> ORGANISM: Homo sapiens

<400> SEQUENCE: 12
cttctacaat gagctgggtg                                                 20

<210> SEQ ID NO 13
<211> LENGTH: 20
<212> TYPE: DNA
<213> ORGANISM: Homo sapiens

<400> SEQUENCE: 13
tcatgaggta gtcagtcagg                                                 20

<210> SEQ ID NO 14
<211> LENGTH: 16
<212> TYPE: DNA
<213> ORGANISM: Homo sapiens

<400> SEQUENCE: 14
ccccgagggc ggcatg                                                     16

<210> SEQ ID NO 15
<211> LENGTH: 16
<212> TYPE: DNA
<213> ORGANISM: Homo sapiens

<400> SEQUENCE: 15
catgccgccc tcgggg                                                     16

<210> SEQ ID NO 16
<211> LENGTH: 16
<212> TYPE: DNA
<213> ORGANISM: Homo sapiens

<400> SEQUENCE: 16
cacacagtag tgcatg                                                     16

<210> SEQ ID NO 17
<211> LENGTH: 16
<212> TYPE: DNA
<213> ORGANISM: Homo sapiens

<400> SEQUENCE: 17
catgcactac tgtgtg                                                     16

<210> SEQ ID NO 18
<211> LENGTH: 16
<212> TYPE: DNA
<213> ORGANISM: Homo sapiens

<400> SEQUENCE: 18
cctttgcaag tgcatc                                                                      16

<210> SEQ ID NO 19
<211> LENGTH: 16
<212> TYPE: DNA
<213> ORGANISM: Homo sapiens

<400> SEQUENCE: 19
gatgcacttg caaagg                                                                      16

<210> SEQ ID NO 20
<211> LENGTH: 2574
<212> TYPE: DNA
<213> ORGANISM: Homo sapiens
<220> FEATURE:
<221> NAME/KEY: CDS
<222> LOCATION: (254)..(1492)

<400> SEQUENCE: 20

```
cctgtttaga cacatggaca acaatcccag cgctacaagg cacacagtcc gcttcttcgt      60
cctcagggtt gccagcgctt cctggaagtc ctgaagctct cgcagtgcag tgagttcatg     120
caccttcttg ccaagcctca gtctttggga tctggggagc ccgcctggtt ttcctccctc     180
cttctgcacg tctgctgggg tctcttcctc tccaggcctt gccgtccccc tggcctctct     240
tcccagctca cac atg aag atg cac ttg caa agg gct ctg gtg gtc ctg       289
            Met Lys Met His Leu Gln Arg Ala Leu Val Val Leu
              1               5                  10 gcc ctg ctg aac ttt gcc acg gtc agc ctc tct ctg tcc act tgc acc      337
Ala Leu Leu Asn Phe Ala Thr Val Ser Leu Ser Leu Ser Thr Cys Thr
           15                  20                  25 acc ttg gac ttc ggc cac atc aag aag aag agg gtg gaa gcc att agg      385
Thr Leu Asp Phe Gly His Ile Lys Lys Lys Arg Val Glu Ala Ile Arg
        30                  35                  40 gga cag atc ttg agc aag ctc agg ctc acc agc ccc cct gag cca acg      433
Gly Gln Ile Leu Ser Lys Leu Arg Leu Thr Ser Pro Pro Glu Pro Thr
45                  50                  55                  60 gtg atg acc cac gtc ccc tat cag gtc ctg gcc ctt tac aac agc acc      481
Val Met Thr His Val Pro Tyr Gln Val Leu Ala Leu Tyr Asn Ser Thr
                65                  70                  75 cgg gag ctg ctg gag gag atg cat ggg gag agg gag gaa ggc tgc acc      529
Arg Glu Leu Leu Glu Glu Met His Gly Glu Arg Glu Glu Gly Cys Thr
            80                  85                  90 cag gaa aac acc gag tcg gaa tac tat gcc aaa gaa atc cat aaa ttc      577
Gln Glu Asn Thr Glu Ser Glu Tyr Tyr Ala Lys Glu Ile His Lys Phe
         95                 100                 105 gac atg atc cag ggg ctg gcg gag cac aac gaa ctg gct gtc tgc cct      625
Asp Met Ile Gln Gly Leu Ala Glu His Asn Glu Leu Ala Val Cys Pro
     110                 115                 120 aaa gga att acc tcc aag gtt ttc cgc ttc aat gtg tcc tca gtg gag      673
Lys Gly Ile Thr Ser Lys Val Phe Arg Phe Asn Val Ser Ser Val Glu
125                 130                 135                 140 aaa aat aga acc aac cta ttc cga gca gaa ttc cgg gtc ttg cgg gtg      721
Lys Asn Arg Thr Asn Leu Phe Arg Ala Glu Phe Arg Val Leu Arg Val
                145                 150                 155 ccc aac ccc agc tct aag cgg aat gag cag agg atc gag ctc ttc cag      769
Pro Asn Pro Ser Ser Lys Arg Asn Glu Gln Arg Ile Glu Leu Phe Gln
            160                 165                 170
```

```
atc ctt cgg cca gat gag cac att gcc aaa cag cgc tat atc ggt ggc      817
Ile Leu Arg Pro Asp Glu His Ile Ala Lys Gln Arg Tyr Ile Gly Gly
        175                 180                 185 aag aat ctg ccc aca cgg ggc act gcc gag tgg ctg tcc ttt gat gtc      865
Lys Asn Leu Pro Thr Arg Gly Thr Ala Glu Trp Leu Ser Phe Asp Val
        190                 195                 200 act gac act gtg cgt gag tgg ctg ttg aga aga gag tcc aac tta ggt      913
Thr Asp Thr Val Arg Glu Trp Leu Leu Arg Arg Glu Ser Asn Leu Gly
205                 210                 215                 220 cta gaa atc agc att cac tgt cca tgt cac acc ttt cag ccc aat gga      961
Leu Glu Ile Ser Ile His Cys Pro Cys His Thr Phe Gln Pro Asn Gly
                225                 230                 235 gat atc ctg gaa aac att cac gag gtg atg gaa atc aaa ttc aaa ggc     1009
Asp Ile Leu Glu Asn Ile His Glu Val Met Glu Ile Lys Phe Lys Gly
        240                 245                 250 gtg gac aat gag gat gac cat ggc cgt gga gat ctg ggg cgc ctc aag     1057
Val Asp Asn Glu Asp Asp His Gly Arg Gly Asp Leu Gly Arg Leu Lys
        255                 260                 265 aag cag aag gat cac cac aac cct cat cta atc ctc atg atg att ccc     1105
Lys Gln Lys Asp His His Asn Pro His Leu Ile Leu Met Met Ile Pro
        270                 275                 280 cca cac cgg ctc gac aac ccg ggc cag ggg ggt cag agg aag aag cgg     1153
Pro His Arg Leu Asp Asn Pro Gly Gln Gly Gly Gln Arg Lys Lys Arg
285                 290                 295                 300 gct ttg gac acc aat tac tgc ttc cgc aac ttg gag gag aac tgc tgt     1201
Ala Leu Asp Thr Asn Tyr Cys Phe Arg Asn Leu Glu Glu Asn Cys Cys
                305                 310                 315 gtg cgc ccc ctc tac att gac ttc cga cag gat ctg ggc tgg aag tgg     1249
Val Arg Pro Leu Tyr Ile Asp Phe Arg Gln Asp Leu Gly Trp Lys Trp
        320                 325                 330 gtc cat gaa cct aag ggc tac tat gcc aac ttc tgc tca ggc cct tgc     1297
Val His Glu Pro Lys Gly Tyr Tyr Ala Asn Phe Cys Ser Gly Pro Cys
        335                 340                 345 cca tac ctc cgc agt gca gac aca acc cac agc acg gtg ctg gga ctg     1345
Pro Tyr Leu Arg Ser Ala Asp Thr Thr His Ser Thr Val Leu Gly Leu
350                 355                 360 tac aac act ctg aac cct gaa gca tct gcc tcg cct tgc tgc gtg ccc     1393
Tyr Asn Thr Leu Asn Pro Glu Ala Ser Ala Ser Pro Cys Cys Val Pro
365                 370                 375                 380 cag gac ctg gag ccc ctg acc atc ctg tac tat gtt ggg agg acc ccc     1441
Gln Asp Leu Glu Pro Leu Thr Ile Leu Tyr Tyr Val Gly Arg Thr Pro
                385                 390                 395 aaa gtg gag cag ctc tcc aac atg gtg gtg aag tct tgt aaa tgt agc     1489
Lys Val Glu Gln Leu Ser Asn Met Val Val Lys Ser Cys Lys Cys Ser
                400                 405                 410 tga gaccccacgt gcgacagaga gagggagag agaaccacca ctgcctgact           1542
gcccgctcct cgggaaacac acaagcaaca aacctcactg agaggcctgg agcccacaac   1602
cttcggctcc gggcaaatgg ctgagatgga ggtttccttt tggaacattt ctttcttgct   1662
ggctctgaga atcacggtgg taagaaagt gtgggtttgg ttagaggaag gctgaactct    1722
tcagaacaca cagactttct gtgacgcaga cagagggat ggggatagag gaaagggatg    1782
gtaagttgag atgttgtgtg gcaatgggat ttgggctacc ctaaagggag aaggaagggc   1842
agagaatggc tgggtcaggg ccagactgga agacacttca gatctgaggt tggatttgct   1902
cattgctgta ccacatctgc tctagggaat ctggattatg ttatacaagg caagcatttt   1962 ttttttttaaa gacaggttac gaagacaaag tcccagaatt gtatctcata ctgtctggga  2022
```

```
ttaagggcaa atctattact tttgcaaact gtcctctaca tcaattaaca tcgtgggtca      2082
ctacagggag aaaatccagg tcatgcagtt cctggcccat caactgtatt gggccttttg      2142
gatatgctga acgcagaaga aagggtggaa atcaaccctc tcctgtctgc cctctgggtc      2202
cctcctctca cctctccctc gatcatattt ccccttggac acttggttag acgccttcca      2262
ggtcaggatg cacatttctg gattgtggtt ccatgcagcc ttggggcatt atgggtcttc      2322
ccccacttcc cctccaagac cctgtgttca tttggtgttc ctggaagcag gtgctacaac      2382
atgtgaggca ttcggggaag ctgcacatgt gccacacagt gacttggccc cagacgcata      2442
gactgaggta taaagacaag tatgaatatt actctcaaaa tctttgtata aataaatatt      2502
tttggggcat cctggatgat ttcatcttct ggaatattgt ttctagaaca gtaaaagcct      2562
tattctaagg tg                                                         2574
```

<210> SEQ ID NO 21
<211> LENGTH: 412
<212> TYPE: PRT
<213> ORGANISM: Homo sapiens

<400> SEQUENCE: 21

```
Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
                20                  25                  30

Gly His Ile Lys Lys Arg Val Glu Ala Ile Arg Gly Gln Ile Leu
            35                  40                  45

Ser Lys Leu Arg Leu Thr Ser Pro Pro Glu Pro Thr Val Met Thr His
    50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
        115                 120                 125

Ser Lys Val Phe Arg Phe Asn Val Ser Ser Val Glu Lys Asn Arg Thr
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
    210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270
```

```
His His Asn Pro His Leu Ile Leu Met Met Ile Pro Pro His Arg Leu
            275                 280                 285

Asp Asn Pro Gly Gln Gly Gly Gln Arg Lys Lys Arg Ala Leu Asp Thr
    290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
                340                 345                 350

Ser Ala Asp Thr Thr His Ser Thr Val Leu Gly Leu Tyr Asn Thr Leu
            355                 360                 365

Asn Pro Glu Ala Ser Ala Ser Pro Cys Cys Val Pro Gln Asp Leu Glu
    370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410

<210> SEQ ID NO 22
<211> LENGTH: 3678
<212> TYPE: DNA
<213> ORGANISM: Homo sapiens
<220> FEATURE:
<221> NAME/KEY: CDS
<222> LOCATION: (29)..(2509)

<400> SEQUENCE: 22
gtgaagacat cgcggggacc gattcacc atg gag ggc gcc ggc ggc gcg aac       52
                                Met Glu Gly Ala Gly Gly Ala Asn
                                  1               5 gac aag aaa aag ata agt tct gaa cgt cga aaa gaa aag tct cga gat     100
Asp Lys Lys Lys Ile Ser Ser Glu Arg Arg Lys Glu Lys Ser Arg Asp
     10                  15                  20 gca gcc aga tct cgg cga agt aaa gaa tct gaa gtt ttt tat gag ctt     148
Ala Ala Arg Ser Arg Arg Ser Lys Glu Ser Glu Val Phe Tyr Glu Leu
25                  30                  35                  40 gct cat cag ttg cca ctt cca cat aat gtg agt tcg cat ctt gat aag     196
Ala His Gln Leu Pro Leu Pro His Asn Val Ser Ser His Leu Asp Lys
                45                  50                  55 gcc tct gtg atg agg ctt acc atc agc tat ttg cgt gtg agg aaa ctt     244
Ala Ser Val Met Arg Leu Thr Ile Ser Tyr Leu Arg Val Arg Lys Leu
            60                  65                  70 ctg gat gct ggt gat ttg gat att gaa gat gac atg aaa gca cag atg     292
Leu Asp Ala Gly Asp Leu Asp Ile Glu Asp Asp Met Lys Ala Gln Met
        75                  80                  85 aat tgc ttt tat ttg aaa gcc ttg gat ggt ttt gtt atg gtt ctc aca     340
Asn Cys Phe Tyr Leu Lys Ala Leu Asp Gly Phe Val Met Val Leu Thr
    90                  95                 100 gat gat ggt gac atg att tac att tct gat aat gtg aac aaa tac atg     388
Asp Asp Gly Asp Met Ile Tyr Ile Ser Asp Asn Val Asn Lys Tyr Met
105                 110                 115                 120 gga tta act cag ttt gaa cta act gga cac agt gtg ttt gat ttt act     436
Gly Leu Thr Gln Phe Glu Leu Thr Gly His Ser Val Phe Asp Phe Thr
                125                 130                 135 cat cca tgt gac cat gag gaa atg aga gaa atg ctt aca cac aga aat     484
His Pro Cys Asp His Glu Glu Met Arg Glu Met Leu Thr His Arg Asn
            140                 145                 150 ggc ctt gtg aaa aag ggt aaa gaa caa aac aca cag cga agc ttt ttt     532
```

```
                Gly Leu Val Lys Lys Gly Lys Glu Gln Asn Thr Gln Arg Ser Phe Phe
                            155                 160                 165 ctc aga atg aag tgt acc cta act agc cga gga aga act atg aac ata         580
Leu Arg Met Lys Cys Thr Leu Thr Ser Arg Gly Arg Thr Met Asn Ile
        170                 175                 180 aag tct gca aca tgg aag gta ttg cac tgc aca ggc att cac gta             628
Lys Ser Ala Thr Trp Lys Val Leu His Cys Thr Gly His Ile His Val
185                 190                 195                 200 tat gat acc aac agt aac caa cct cag tgt ggg tat aag aaa cca cct         676
Tyr Asp Thr Asn Ser Asn Gln Pro Gln Cys Gly Tyr Lys Lys Pro Pro
                    205                 210                 215 atg acc tgc ttg gtg ctg att tgt gaa ccc att cct cac cca tca aat         724
Met Thr Cys Leu Val Leu Ile Cys Glu Pro Ile Pro His Pro Ser Asn
            220                 225                 230 att gaa att cct tta gat agc aag act ttc ctc agt cga cac agc ctg         772
Ile Glu Ile Pro Leu Asp Ser Lys Thr Phe Leu Ser Arg His Ser Leu
        235                 240                 245 gat atg aaa ttt tct tat tgt gat gaa aga att acc gaa ttg atg gga         820
Asp Met Lys Phe Ser Tyr Cys Asp Glu Arg Ile Thr Glu Leu Met Gly
    250                 255                 260 tat gag cca gaa gaa ctt tta ggc cgc tca att tat gaa tat tat cat         868
Tyr Glu Pro Glu Glu Leu Leu Gly Arg Ser Ile Tyr Glu Tyr Tyr His
265                 270                 275                 280 gct ttg gac tct gat cat ctg acc aaa act cat cat gat atg ttt act         916
Ala Leu Asp Ser Asp His Leu Thr Lys Thr His His Asp Met Phe Thr
                    285                 290                 295 aaa gga caa gtc acc aca gga cag tac agg atg ctt gcc aaa aga ggt         964
Lys Gly Gln Val Thr Thr Gly Gln Tyr Arg Met Leu Ala Lys Arg Gly
            300                 305                 310 gga tat gtc tgg gtt gaa act caa gca act gtc ata tat aac acc aag         1012
Gly Tyr Val Trp Val Glu Thr Gln Ala Thr Val Ile Tyr Asn Thr Lys
        315                 320                 325 aat tct caa cca cag tgc att gta tgt gtg aat tac gtt gtg agt ggt         1060
Asn Ser Gln Pro Gln Cys Ile Val Cys Val Asn Tyr Val Val Ser Gly
    330                 335                 340 att att cag cac gac ttg att ttc tcc ctt caa caa aca gaa tgt gtc         1108
Ile Ile Gln His Asp Leu Ile Phe Ser Leu Gln Gln Thr Glu Cys Val
345                 350                 355                 360 ctt aaa ccg gtt gaa tct tca gat atg aaa atg act cag cta ttc acc         1156
Leu Lys Pro Val Glu Ser Ser Asp Met Lys Met Thr Gln Leu Phe Thr
                    365                 370                 375 aaa gtt gaa tca gaa gat aca agt agc ctc ttt gac aaa ctt aag aag         1204
Lys Val Glu Ser Glu Asp Thr Ser Ser Leu Phe Asp Lys Leu Lys Lys
            380                 385                 390 gaa cct gat gct tta act ttg ctg gcc cca gcc gct gga gac aca atc         1252
Glu Pro Asp Ala Leu Thr Leu Leu Ala Pro Ala Ala Gly Asp Thr Ile
        395                 400                 405 ata tct tta gat ttt ggc agc aac gac aca gaa act gat gac cag caa         1300
Ile Ser Leu Asp Phe Gly Ser Asn Asp Thr Glu Thr Asp Asp Gln Gln
    410                 415                 420 ctt gag gaa gta cca tta tat aat gat gta atg ctc ccc tca ccc aac         1348
Leu Glu Glu Val Pro Leu Tyr Asn Asp Val Met Leu Pro Ser Pro Asn
425                 430                 435                 440 gaa aaa tta cag aat ata aat ttg gca atg tct cca tta ccc acc gct         1396
Glu Lys Leu Gln Asn Ile Asn Leu Ala Met Ser Pro Leu Pro Thr Ala
                    445                 450                 455 gaa acg cca aag cca ctt cga agt agt gct gac cct gca ctc aat caa         1444
Glu Thr Pro Lys Pro Leu Arg Ser Ser Ala Asp Pro Ala Leu Asn Gln
            460                 465                 470
```

-continued

```
gaa gtt gca tta aaa tta gaa cca aat cca gag tca ctg gaa ctt tct       1492
Glu Val Ala Leu Lys Leu Glu Pro Asn Pro Glu Ser Leu Glu Leu Ser
            475                 480                 485 ttt acc atg ccc cag att cag gat cag aca cct agt cct tcc gat gga       1540
Phe Thr Met Pro Gln Ile Gln Asp Gln Thr Pro Ser Pro Ser Asp Gly
        490                 495                 500 agc act aga caa agt tca cct gag cct aat agt ccc agt gaa tat tgt       1588
Ser Thr Arg Gln Ser Ser Pro Glu Pro Asn Ser Pro Ser Glu Tyr Cys
505                 510                 515                 520 ttt tat gtg gat agt gat atg gtc aat gaa ttc aag ttg gaa ttg gta       1636
Phe Tyr Val Asp Ser Asp Met Val Asn Glu Phe Lys Leu Glu Leu Val
                525                 530                 535 gaa aaa ctt ttt gct gaa gac aca gaa gca aag aac cca ttt tct act       1684
Glu Lys Leu Phe Ala Glu Asp Thr Glu Ala Lys Asn Pro Phe Ser Thr
            540                 545                 550 cag gac aca gat tta gac ttg gag atg tta gct ccc tat atc cca atg       1732
Gln Asp Thr Asp Leu Asp Leu Glu Met Leu Ala Pro Tyr Ile Pro Met
        555                 560                 565 gat gat gac ttc cag tta cgt tcc ttc gat cag ttg tca cca tta gaa       1780
Asp Asp Asp Phe Gln Leu Arg Ser Phe Asp Gln Leu Ser Pro Leu Glu
570                 575                 580 agc agt tcc gca agc cct gaa agc gca agt cct caa agc aca gtt aca       1828
Ser Ser Ser Ala Ser Pro Glu Ser Ala Ser Pro Gln Ser Thr Val Thr
585                 590                 595                 600 gta ttc cag cag act caa ata caa gaa cct act gct aat gcc acc act       1876
Val Phe Gln Gln Thr Gln Ile Gln Glu Pro Thr Ala Asn Ala Thr Thr
            605                 610                 615 acc act gcc acc act gat gaa tta aaa aca gtg aca aaa gac cgt atg       1924
Thr Thr Ala Thr Thr Asp Glu Leu Lys Thr Val Thr Lys Asp Arg Met
        620                 625                 630 gaa gac att aaa ata ttg att gca tct cca tct cct acc cac ata cat       1972
Glu Asp Ile Lys Ile Leu Ile Ala Ser Pro Ser Pro Thr His Ile His
635                 640                 645 aaa gaa act act agt gcc aca tca tca cca tat aga gat act caa agt       2020
Lys Glu Thr Thr Ser Ala Thr Ser Ser Pro Tyr Arg Asp Thr Gln Ser
            650                 655                 660 cgg aca gcc tca cca aac aga gca gga aaa gga gtc ata gaa cag aca       2068
Arg Thr Ala Ser Pro Asn Arg Ala Gly Lys Gly Val Ile Glu Gln Thr
665                 670                 675                 680 gaa aaa tct cat cca aga agc cct aac gtg tta tct gtc gct ttg agt       2116
Glu Lys Ser His Pro Arg Ser Pro Asn Val Leu Ser Val Ala Leu Ser
                685                 690                 695 caa aga act aca gtt cct gag gaa gaa cta aat cca aag ata cta gct       2164
Gln Arg Thr Thr Val Pro Glu Glu Glu Leu Asn Pro Lys Ile Leu Ala
            700                 705                 710 ttg cag aat gct cag aga aag cga aaa atg gaa cat gat ggt tca ctt       2212
Leu Gln Asn Ala Gln Arg Lys Arg Lys Met Glu His Asp Gly Ser Leu
        715                 720                 725 ttt caa gca gta gga att gga aca tta tta cag cag cca gac gat cat       2260
Phe Gln Ala Val Gly Ile Gly Thr Leu Leu Gln Gln Pro Asp Asp His
730                 735                 740 gca gct act aca tca ctt tct tgg aaa cgt gta aaa gga tgc aaa tct       2308
Ala Ala Thr Thr Ser Leu Ser Trp Lys Arg Val Lys Gly Cys Lys Ser
745                 750                 755                 760 agt gaa cag aat gga atg gag caa aag aca att att tta ata ccc tct       2356
Ser Glu Gln Asn Gly Met Glu Gln Lys Thr Ile Ile Leu Ile Pro Ser
                765                 770                 775 gat tta gca tgt aga ctg ctg ggg caa tca atg gat gaa agt gga tta       2404
Asp Leu Ala Cys Arg Leu Leu Gly Gln Ser Met Asp Glu Ser Gly Leu
            780                 785                 790
```

-continued

```
cca cag ctg acc agt tat gat tgt gaa gtt aat gct cct ata caa ggc       2452
Pro Gln Leu Thr Ser Tyr Asp Cys Glu Val Asn Ala Pro Ile Gln Gly
            795                 800                 805 agc aga aac cta ctg cag ggt gaa gaa tta ctc aga gct ttg gat caa       2500
Ser Arg Asn Leu Leu Gln Gly Glu Glu Leu Leu Arg Ala Leu Asp Gln
    810                 815                 820 gtt aac tga gcttttctt aatttcattc cttttttgg acactggtgg                 2549
Val Asn
825 ctcactacct aaagcagtct atttatattt tctacatcta attttagaag cctggctaca     2609
atactgcaca aacttggtta gttcaatttt tgatccccct tctacttaat ttacattaat     2669
gctctttttt agtatgttct ttaatgctgg atcacagaca gctcattttc tcagttttt     2729
ggtatttaaa ccattgcatt gcagtagcat cattttaaaa aatgcacctt tttatttatt    2789
tattttggc tagggagttt atccctttt cgaattattt ttaagaagat gccaatataa       2849
tttttgtaag aaggcagtaa cctttcatca tgatcatagg cagttgaaaa attttacac     2909
cttttttttc acattttaca taaataataa tgctttgcca gcagtacgtg gtagccacaa     2969
ttgcacaata tattttctta aaaatacca gcagttactc atggaatata ttctgcgttt      3029
ataaaactag tttttaagaa gaatttttt ttggcctatg aaattgttaa acctggaaca      3089
tgacattgtt aatcatataa taatgattct taaatgctgt atggtttatt atttaaatgg    3149
gtaaagccat ttcataata tagaaagata tgcatatatc tagaaggtat gtggcattta     3209
tttggataaa attctcaatt cagagaaatc atctgatgtt tctatagtca ctttgccagc    3269
tcaaaagaaa acaataccct atgtagttgt ggaagtttat gctaatattg tgtaactgat    3329
attaaaccta aatgttctgc ctaccctgtt ggtataaaga tattttgagc agactgtaaa    3389
caagaaaaaa aaaatcatgc attcttagca aaattgccta gtatgttaat ttgctcaaaa    3449
tacaatgttt gattttatgc actttgtcgc tattaacatc cttttttca tgtagatttc      3509
aataattgag taattttaga agcattattt taggaatata tagttgtcac agtaaatatc    3569
ttgtttttc tatgtacatt gtacaaattt ttcattcctt ttgctctttg tggttggatc      3629
taacactaac tgtattgttt tgttacatca aataaacatc ttctgtgga                3678
```

<210> SEQ ID NO 23
<211> LENGTH: 826
<212> TYPE: PRT
<213> ORGANISM: Homo sapiens

<400> SEQUENCE: 23

```
Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110
```

```
Ser Asp Asn Val Asn Lys Tyr Met Gly Leu Thr Gln Phe Glu Leu Thr
        115                 120                 125
Gly His Ser Val Phe Asp Phe Thr His Pro Cys Asp His Glu Glu Met
        130                 135                 140
Arg Glu Met Leu Thr His Arg Asn Gly Leu Val Lys Lys Gly Lys Glu
145                 150                 155                 160
Gln Asn Thr Gln Arg Ser Phe Phe Leu Arg Met Lys Cys Thr Leu Thr
        165                 170                 175
Ser Arg Gly Arg Thr Met Asn Ile Lys Ser Ala Thr Trp Lys Val Leu
        180                 185                 190
His Cys Thr Gly His Ile His Val Tyr Asp Thr Asn Ser Asn Gln Pro
        195                 200                 205
Gln Cys Gly Tyr Lys Lys Pro Pro Met Thr Cys Leu Val Leu Ile Cys
        210                 215                 220
Glu Pro Ile Pro His Pro Ser Asn Ile Glu Ile Pro Leu Asp Ser Lys
225                 230                 235                 240
Thr Phe Leu Ser Arg His Ser Leu Asp Met Lys Phe Ser Tyr Cys Asp
        245                 250                 255
Glu Arg Ile Thr Glu Leu Met Gly Tyr Glu Pro Glu Glu Leu Leu Gly
        260                 265                 270
Arg Ser Ile Tyr Glu Tyr Tyr His Ala Leu Asp Ser Asp His Leu Thr
        275                 280                 285
Lys Thr His His Asp Met Phe Thr Lys Gly Gln Val Thr Thr Gly Gln
        290                 295                 300
Tyr Arg Met Leu Ala Lys Arg Gly Gly Tyr Val Trp Val Glu Thr Gln
305                 310                 315                 320
Ala Thr Val Ile Tyr Asn Thr Lys Asn Ser Gln Pro Gln Cys Ile Val
        325                 330                 335
Cys Val Asn Tyr Val Val Ser Gly Ile Ile Gln His Asp Leu Ile Phe
        340                 345                 350
Ser Leu Gln Gln Thr Glu Cys Val Leu Lys Pro Val Glu Ser Ser Asp
        355                 360                 365
Met Lys Met Thr Gln Leu Phe Thr Lys Val Glu Ser Glu Asp Thr Ser
        370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
        405                 410                 415
Asp Thr Glu Thr Asp Asp Gln Gln Leu Glu Glu Val Pro Leu Tyr Asn
        420                 425                 430
Asp Val Met Leu Pro Ser Pro Asn Glu Lys Leu Gln Asn Ile Asn Leu
        435                 440                 445
Ala Met Ser Pro Leu Pro Thr Ala Glu Thr Pro Lys Pro Leu Arg Ser
        450                 455                 460
Ser Ala Asp Pro Ala Leu Asn Gln Glu Val Ala Leu Lys Leu Glu Pro
465                 470                 475                 480
Asn Pro Glu Ser Leu Glu Leu Ser Phe Thr Met Pro Gln Ile Gln Asp
        485                 490                 495
Gln Thr Pro Ser Pro Ser Asp Gly Ser Thr Arg Gln Ser Ser Pro Glu
        500                 505                 510
Pro Asn Ser Pro Ser Glu Tyr Cys Phe Tyr Val Asp Ser Asp Met Val
        515                 520                 525
```

```
-continued

Asn Glu Phe Lys Leu Glu Leu Val Glu Lys Leu Phe Ala Glu Asp Thr
            530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
                580                 585                 590

Ala Ser Pro Gln Ser Thr Val Thr Val Phe Gln Gln Thr Gln Ile Gln
                595                 600                 605

Glu Pro Thr Ala Asn Ala Thr Thr Thr Thr Ala Thr Thr Asp Glu Leu
            610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
                660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
                740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
            770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 24
<211> LENGTH: 8
<212> TYPE: DNA
<213> ORGANISM: Homo sapiens

<400> SEQUENCE: 24 bacgtssk                                                                8
```